US009061042B2

(12) United States Patent
Yagi et al.

(10) Patent No.: US 9,061,042 B2
(45) Date of Patent: Jun. 23, 2015

(54) COMPOSITION FOR SUPPRESSING EXPRESSION OF TARGET GENE

(75) Inventors: Nobuhiro Yagi, Shizuoka (JP); Junichi Enokizono, Shizuoka (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 327 days.

(21) Appl. No.: 13/017,562

(22) Filed: Jan. 31, 2011

(65) Prior Publication Data

US 2011/0182980 A1 Jul. 28, 2011

Related U.S. Application Data

(63) Continuation-in-part of application No. PCT/JP2009/063685, filed on Jul. 31, 2009.

(30) Foreign Application Priority Data

Aug. 1, 2008 (JP) ................................. 2008-200182

(51) Int. Cl.

| C12N 15/11 | (2006.01) |
|---|---|
| A61K 31/7105 | (2006.01) |
| A61K 9/00 | (2006.01) |
| A61K 9/127 | (2006.01) |
| A61K 31/712 | (2006.01) |
| A61K 31/713 | (2006.01) |
| C12N 15/113 | (2010.01) |

(52) U.S. Cl.

CPC ........... *A61K 31/7105* (2013.01); *A61K 9/0019* (2013.01); *A61K 9/1271* (2013.01); *A61K 31/712* (2013.01); *A61K 31/713* (2013.01); *C12N 15/1135* (2013.01); *Y10T 436/143333* (2015.01); *C12N 2310/14* (2013.01)

(58) Field of Classification Search

CPC .......................... C12N 15/11; C12N 2310/14
See application file for complete search history.

(56) References Cited

U.S. PATENT DOCUMENTS

| 2002/0132788 | A1 | 9/2002 | Lewis et al. | |
|---|---|---|---|---|
| 2003/0139363 | A1 | 7/2003 | Kay et al. | |
| 2003/0153519 | A1 | 8/2003 | Kay et al. | |
| 2004/0022938 | A1 | 2/2004 | Kato et al. | |
| 2006/0211642 | A1* | 9/2006 | McSwiggen et al. | 514/44 |
| 2007/0135372 | A1 | 6/2007 | MacLachlan et al. | |
| 2009/0011003 | A1 | 1/2009 | Yamauchi et al. | |

FOREIGN PATENT DOCUMENTS

| JP | 2002-501511 | 1/2002 |
|---|---|---|
| JP | 2002-508765 | 3/2002 |
| WO | 98/51278 | 11/1998 |
| WO | 98/58630 | 12/1998 |
| WO | 02/28367 | 4/2002 |
| WO | 03/010180 | 2/2003 |
| WO | 2006/080118 | 8/2006 |

OTHER PUBLICATIONS

Lewis D et al. "Efficient delivery of siRNA for inhibition of gene expression in postnatal mice", Nature Genetics, vol. 32, No. 1, 2002, pp. 107-108.
Haibin X et al. "siRNA-mediated gene silencing in vitro and in vivo", Nature Biotechnology, vol. 20, No. 10, 2002, pp. 1006-1010.
Semple S et al. "Efficient encapsulation of antisense oligonucleotides in lipid vesicles using ionizable aminolipids: formation of novel small multilamellar vesicle structures", Biochimica et Biophysica Acta, vol. 1510, 2001, pp. 152-166.
Shin D et al. "Immunostimulatory properties and antiviral activity of modified HBV-specific siRNAs", Biochemical and Biophysical Research Communications, vol. 364, No. 3, 2007, pp. 436-442.
Allerson C et al. "Fully 2-Modified Oligonucleotide Duplexes with Improved in Vitro Potency and Stability Compared to Unmodified Small Interfering RNA", J. Med. Chem., vol. 48, No. 4, 2005, pp. 901-904.
Layzer J et al. "In vivo activity of nuclease-resistant siRNAs", RNA, vol. 10, No. 5, 2004, pp. 766-771.
Chiu Y et al. "siRNA function in RNAi: A chemical modification analysis", RNA, vol. 9, No. 9, 2003, pp. 1034-1048.
Semple S et al. "Immunogenicity and Rapid Blood Clearance of Liposomes Containing Polyethylene Glycol-Lipid Conjugates and Nucleic Acid", The Journal of Pharmacology and Experimental Therapeutics, vol. 312, No. 3, 2005, pp. 1020-1026.
Extended European Search Report issued Dec. 11, 2012 in European Application No. 09803053.9.

* cited by examiner

*Primary Examiner* — Jon E Angell
(74) *Attorney, Agent, or Firm* — Wenderoth, Lind & Ponack, L.L.P.

(57) ABSTRACT

An object of the present invention is to provide a composition for suppressing expression of a target gene, and the like. A composition comprising an RNA-encapsulated liposome, wherein the RNA contains a sequence consisting of 15 to 30 contiguous bases of a target gene mRNA (hereinafter, sequence X) and a base sequence (hereinafter, complementary sequence X') complementary to the sequence X, 1 to 90% of all sugars binding to the bases of the sequence X and the complementary sequence X' being ribose substituted by a modifying group at 2' position, and the lipid particle being capable of reaching a tissue or an organ containing an expression site of the target gene is provide.

10 Claims, 4 Drawing Sheets

SEQUENCE LISTING

```
<160> NUMBER OF SEQ ID NOS: 29

<210> SEQ ID NO 1
<211> LENGTH: 21
<212> TYPE: DNA
<213> ORGANISM: Artificial Sequence
<220> FEATURE:
<223> OTHER INFORMATION: Synthetic construct; siRNA sense of exp.1
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (2)..(2)
<223> OTHER INFORMATION: n = uracil
<220> FEATURE:
<221> NAME/KEY: modified_base
<222> LOCATION: (2)..(2)
<223> OTHER INFORMATION: um
<220> FEATURE:
```

```
<221> NAME/KEY: modified_base
<222> LOCATION: (4)..(4)
<223> OTHER INFORMATION: am
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: n = uracil
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (10)..(10)
<223> OTHER INFORMATION: am
<220> FEATURE:
<221> NAME/KEY: modified_base
<222> LOCATION: (12)..(12)
<223> OTHER INFORMATION: am
<220> FEATURE:
<221> NAME/KEY: misc_feature
<222> LOCATION: (13)..(13)
<223> OTHER INFORMATION: n = uracil
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (16)..(16)
<223> OTHER INFORMATION: cm
<220> FEATURE:
<221> NAME/KEY: misc_feature
<222> LOCATION: (17)..(17)
<223> OTHER INFORMATION: n = uracil
<220> FEATURE:
<221> NAME/KEY: modified_base
<222> LOCATION: (18)..(18)
<223> OTHER INFORMATION: gm

<400> SEQUENCE: 1
gngaagncaa cangccngct t                                             21

<210> SEQ ID NO 2
<211> LENGTH: 21
<212> TYPE: DNA
<213> ORGANISM: Artificial Sequence
<220> FEATURE:
<223> OTHER INFORMATION: Synthetic construct; siRNA antisense of exp.1
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (3)..(3)
<223> OTHER INFORMATION: am
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: am
<220> FEATURE:
<221> NAME/KEY: misc_feature
<222> LOCATION: (8)..(8)
<223> OTHER INFORMATION: n = uracil
```

```
<220> FEATURE:
<221> NAME/KEY: modified_base
<222> LOCATION: (9)..(9)
<223> OTHER INFORMATION: gm
<220> FEATURE:
<221> NAME/KEY: misc_feature
<222> LOCATION: (10)..(10)
<223> OTHER INFORMATION: n = uracil
<220> FEATURE:
<221> NAME/KEY: misc_feature
<222> LOCATION: (11)..(11)
<223> OTHER INFORMATION: n = uracil
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: am
<220> FEATURE:
<221> NAME/KEY: misc_feature
<222> LOCATION: (15)..(15)
<223> OTHER INFORMATION: n = uracil
<220> FEATURE:
<221> NAME/KEY: modified_base
<222> LOCATION: (15)..(15)
<223> OTHER INFORMATION: um
<220> FEATURE:
<221> NAME/KEY: misc_feature
<222> LOCATION: (16)..(16)
<223> OTHER INFORMATION: n = uracil
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (19)..(19)
<223> OTHER INFORMATION: cm

<400> SEQUENCE: 2
gcaggcangn ngacnncact t                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic construct; siRNA sense of com.1
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (2)..(2)
<223> OTHER INFORMATION: n = uracil
<220> FEATURE:
<221> NAME/KEY: misc_feature
<222> LOCATION: (7)..(7)
<223> OTHER INFORMATION: n = uracil
<220> FEATURE:
<221> NAME/KEY: misc_feature
<222> LOCATION: (13)..(13)
<223> OTHER INFORMATION: n = uracil
<220> FEATURE:
<221> NAME/KEY: misc_feature
<222> LOCATION: (17)..(17)
<223> OTHER INFORMATION: n = uracil

<400> SEQUENCE: 3
gngaagncaa cangccngct t                                              21

<210> SEQ ID NO 4
```

```
<211> LENGTH: 21
<212> TYPE: DNA
<213> ORGANISM: Artificial Sequence
<220> FEATURE:
<223> OTHER INFORMATION: Synthetic construct; siRNA antisense of com.1
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (8)..(8)
<223> OTHER INFORMATION: n = uracil
<220> FEATURE:
<221> NAME/KEY: misc_feature
<222> LOCATION: (10)..(10)
<223> OTHER INFORMATION: n = uracil
<220> FEATURE:
<221> NAME/KEY: misc_feature
<222> LOCATION: (11)..(11)
<223> OTHER INFORMATION: n = uracil
<220> FEATURE:
<221> NAME/KEY: misc_feature
<222> LOCATION: (15)..(15)
<223> OTHER INFORMATION: n = uracil
<220> FEATURE:
<221> NAME/KEY: misc_feature
<222> LOCATION: (16)..(16)
<223> OTHER INFORMATION: n = uracil

<400> SEQUENCE: 4
gcaggcangn ngacnncact t                                              21

<210> SEQ ID NO 5
<211> LENGTH: 20
<212> TYPE: DNA
<213> ORGANISM: Artificial Sequence
<220> FEATURE:
<223> OTHER INFORMATION: Synthetic construct; IS for siRNA sense of
      exp.1
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (2)..(2)
<223> OTHER INFORMATION: n = uracil
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (4)..(4)
<223> OTHER INFORMATION: am
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: n = uracil
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (10)..(10)
<223> OTHER INFORMATION: am
<220> FEATURE:
<221> NAME/KEY: modified_base
<222> LOCATION: (12)..(12)
<223> OTHER INFORMATION: am
<220> FEATURE:
```

```
<221> NAME/KEY: misc_feature
<222> LOCATION: (13)..(13)
<223> OTHER INFORMATION: n = uracil
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (16)..(16)
<223> OTHER INFORMATION: cm
<220> FEATURE:
<221> NAME/KEY: misc_feature
<222> LOCATION: (17)..(17)
<223> OTHER INFORMATION: n = uracil
<220> FEATURE:
<221> NAME/KEY: modified_base
<222> LOCATION: (18)..(18)
<223> OTHER INFORMATION: gm

<400> SEQUENCE: 5
gngaagncaa cangccngct                                                 20

<210> SEQ ID NO 6
<211> LENGTH: 20
<212> TYPE: DNA
<213> ORGANISM: Artificial Sequence
<220> FEATURE:
<223> OTHER INFORMATION: Synthetic construct; IS for siRNA antisense of
      exp.1
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (3)..(3)
<223> OTHER INFORMATION: am
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: am
<220> FEATURE:
<221> NAME/KEY: misc_feature
<222> LOCATION: (8)..(8)
<223> OTHER INFORMATION: n = uracil
<220> FEATURE:
<221> NAME/KEY: modified_base
<222> LOCATION: (9)..(9)
<223> OTHER INFORMATION: gm
<220> FEATURE:
<221> NAME/KEY: misc_feature
<222> LOCATION: (10)..(10)
<223> OTHER INFORMATION: n = uracil
<220> FEATURE:
<221> NAME/KEY: misc_feature
<222> LOCATION: (11)..(11)
<223> OTHER INFORMATION: n = uracil
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: am
<220> FEATURE:
<221> NAME/KEY: misc_feature
<222> LOCATION: (15)..(15)
```

```
<223> OTHER INFORMATION: n = uracil
<220> FEATURE:
<221> NAME/KEY: modified_base
<222> LOCATION: (15)..(15)
<223> OTHER INFORMATION: um
<220> FEATURE:
<221> NAME/KEY: misc_feature
<222> LOCATION: (16)..(16)
<223> OTHER INFORMATION: n = uracil
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (19)..(19)
<223> OTHER INFORMATION: cm

<400> SEQUENCE: 6
gcaggcangn ngacnncact                                           20

<210> SEQ ID NO 7
<211> LENGTH: 20
<212> TYPE: DNA
<213> ORGANISM: Artificial Sequence
<220> FEATURE:
<223> OTHER INFORMATION: Synthetic construct; IS for siRNA sense of
      com.1
<220> FEATURE:
<221> NAME/KEY: misc_feature
<222> LOCATION: (1)..(18)
<223> OTHER INFORMATION: RNA
<220> FEATURE:
<221> NAME/KEY: misc_feature
<222> LOCATION: (2)..(2)
<223> OTHER INFORMATION: n = uracil
<220> FEATURE:
<221> NAME/KEY: misc_feature
<222> LOCATION: (7)..(7)
<223> OTHER INFORMATION: n = uracil
<220> FEATURE:
<221> NAME/KEY: misc_feature
<222> LOCATION: (13)..(13)
<223> OTHER INFORMATION: n = uracil
<220> FEATURE:
<221> NAME/KEY: misc_feature
<222> LOCATION: (17)..(17)
<223> OTHER INFORMATION: n = uracil

<400> SEQUENCE: 7
gngaagncaa cangccngtt                                           20

<210> SEQ ID NO 8
<211> LENGTH: 20
<212> TYPE: DNA
<213> ORGANISM: Artificial Sequence
<220> FEATURE:
<223> OTHER INFORMATION: Synthetic construct; IS for siRNA antisense of
      com.1
<220> FEATURE:
<221> NAME/KEY: misc_feature
<222> LOCATION: (1)..(18)
<223> OTHER INFORMATION: RNA
<220> FEATURE:
<221> NAME/KEY: misc_feature
<222> LOCATION: (7)..(7)
<223> OTHER INFORMATION: n = uracil
<220> FEATURE:
<221> NAME/KEY: misc_feature
<222> LOCATION: (9)..(9)
<223> OTHER INFORMATION: n = uracil
<220> FEATURE:
<221> NAME/KEY: misc_feature
<222> LOCATION: (10)..(10)
<223> OTHER INFORMATION: n = uracil
```

-continued

```
<220> FEATURE:
<221> NAME/KEY: misc_feature
<222> LOCATION: (14)..(14)
<223> OTHER INFORMATION: n = uracil
<220> FEATURE:
<221> NAME/KEY: misc_feature
<222> LOCATION: (15)..(15)
<223> OTHER INFORMATION: n = uracil

<400> SEQUENCE: 8
caggcangnn gacnncactt                                          20

<210> SEQ ID NO 9
<211> LENGTH: 21
<212> TYPE: DNA
<213> ORGANISM: Artificial Sequence
<220> FEATURE:
<223> OTHER INFORMATION: Synthetic construct; siRNA sense of exp.2
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (2)..(2)
<223> OTHER INFORMATION: am
<220> FEATURE:
<221> NAME/KEY: modified_base
<222> LOCATION: (4)..(4)
<223> OTHER INFORMATION: gm
<220> FEATURE:
<221> NAME/KEY: misc_feature
<222> LOCATION: (5)..(5)
<223> OTHER INFORMATION: n = uracil
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (8)..(8)
<223> OTHER INFORMATION: cm
<220> FEATURE:
<221> NAME/KEY: misc_feature
<222> LOCATION: (10)..(10)
<223> OTHER INFORMATION: n = uracil
<220> FEATURE:
<221> NAME/KEY: modified_base
<222> LOCATION: (10)..(10)
<223> OTHER INFORMATION: um
<220> FEATURE:
<221> NAME/KEY: misc_feature
<222> LOCATION: (12)..(12)
<223> OTHER INFORMATION: n = uracil
<220> FEATURE:
<221> NAME/KEY: modified_base
<222> LOCATION: (12)..(12)
<223> OTHER INFORMATION: um
<220> FEATURE:
<221> NAME/KEY: misc_feature
<222> LOCATION: (13)..(13)
<223> OTHER INFORMATION: n = uracil
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (18)..(18)
<223> OTHER INFORMATION: am

<400> SEQUENCE: 9
```

-continued gaagngacan cnncagcaat t                                                    21

<210> SEQ ID NO 10
<211> LENGTH: 21
<212> TYPE: DNA
<213> ORGANISM: Artificial Sequence
<220> FEATURE:
<223> OTHER INFORMATION: Synthetic construct; siRNA antisense of exp.2
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (1)..(1)
<223> OTHER INFORMATION: n = uracil
<220> FEATURE:
<221> NAME/KEY: modified_base
<222> LOCATION: (1)..(1)
<223> OTHER INFORMATION: um
<220> FEATURE:
<221> NAME/KEY: misc_feature
<222> LOCATION: (2)..(2)
<223> OTHER INFORMATION: n = uracil
<220> FEATURE:
<221> NAME/KEY: modified_base
<222> LOCATION: (3)..(3)
<223> OTHER INFORMATION: gm
<220> FEATURE:
<221> NAME/KEY: misc_feature
<222> LOCATION: (5)..(5)
<223> OTHER INFORMATION: n = uracil
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (7)..(7)
<223> OTHER INFORMATION: am
<220> FEATURE:
<221> NAME/KEY: modified_base
<222> LOCATION: (9)..(9)
<223> OTHER INFORMATION: gm
<220> FEATURE:
<221> NAME/KEY: misc_feature
<222> LOCATION: (11)..(11)
<223> OTHER INFORMATION: n = uracil
<220> FEATURE:
<221> NAME/KEY: modified_base
<222> LOCATION: (11)..(11)
<223> OTHER INFORMATION: um
<220> FEATURE:
<221> NAME/KEY: misc_feature
<222> LOCATION: (13)..(13)
<223> OTHER INFORMATION: n = uracil
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (15)..(15)
<223> OTHER INFORMATION: am
<220> FEATURE:
<221> NAME/KEY: misc_feature
<222> LOCATION: (17)..(17)
<223> OTHER INFORMATION: n = uracil
<220> FEATURE:
<221> NAME/KEY: modified_base
<222> LOCATION: (17)..(17)
<223> OTHER INFORMATION: um
<220> FEATURE:
<221> NAME/KEY: misc_feature
<222> LOCATION: (18)..(18)
<223> OTHER INFORMATION: n = uracil
<220> FEATURE:
<221> NAME/KEY: modified_base
<222> LOCATION: (19)..(19)
<223> OTHER INFORMATION: cm

<400> SEQUENCE: 10
nngcngaaga ngncacnnct t                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic construct; siRNA sense of exp.3
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (2)..(2)
<223> OTHER INFORMATION: am
<220> FEATURE:
<221> NAME/KEY: modified_base
<222> LOCATION: (4)..(4)
<223> OTHER INFORMATION: gm
<220> FEATURE:
<221> NAME/KEY: misc_feature
<222> LOCATION: (5)..(5)
<223> OTHER INFORMATION: n = uracil
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (8)..(8)
<223> OTHER INFORMATION: cm
<220> FEATURE:
<221> NAME/KEY: misc_feature
<222> LOCATION: (10)..(10)
<223> OTHER INFORMATION: n = uracil
<220> FEATURE:
<221> NAME/KEY: modified_base
<222> LOCATION: (10)..(10)
<223> OTHER INFORMATION: um
<220> FEATURE:
<221> NAME/KEY: misc_feature
<222> LOCATION: (12)..(12)
<223> OTHER INFORMATION: n = uracil
<220> FEATURE:
<221> NAME/KEY: modified_base
<222> LOCATION: (12)..(12)
<223> OTHER INFORMATION: um
<220> FEATURE:
<221> NAME/KEY: misc_feature
<222> LOCATION: (13)..(13)
<223> OTHER INFORMATION: n = uracil
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (18)..(18)
<223> OTHER INFORMATION: am

<400> SEQUENCE: 11
gaagngacan cnncagcaat t                                              21

<210> SEQ ID NO 12
<211> LENGTH: 21
<212> TYPE: DNA

```
<213> ORGANISM: Artificial Sequence
<220> FEATURE:
<223> OTHER INFORMATION: Synthetic construct; siRNA antisense of exp.3
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (1)..(1)
<223> OTHER INFORMATION: n = uracil
<220> FEATURE:
<221> NAME/KEY: misc_feature
<222> LOCATION: (2)..(2)
<223> OTHER INFORMATION: n = uracil
<220> FEATURE:
<221> NAME/KEY: misc_feature
<222> LOCATION: (5)..(5)
<223> OTHER INFORMATION: n = uracil
<220> FEATURE:
<221> NAME/KEY: misc_feature
<222> LOCATION: (11)..(11)
<223> OTHER INFORMATION: n = uracil
<220> FEATURE:
<221> NAME/KEY: misc_feature
<222> LOCATION: (13)..(13)
<223> OTHER INFORMATION: n = uracil
<220> FEATURE:
<221> NAME/KEY: misc_feature
<222> LOCATION: (17)..(17)
<223> OTHER INFORMATION: n = uracil
<220> FEATURE:
<221> NAME/KEY: misc_feature
<222> LOCATION: (18)..(18)
<223> OTHER INFORMATION: n = uracil

<400> SEQUENCE: 12
nngcngaaga ngncacnnct t                                               21

<210> SEQ ID NO 13
<211> LENGTH: 21
<212> TYPE: DNA
<213> ORGANISM: Artificial Sequence
<220> FEATURE:
<223> OTHER INFORMATION: Synthetic construct; siRNA sense of com.2
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (5)..(5)
<223> OTHER INFORMATION: n = uracil
<220> FEATURE:
<221> NAME/KEY: misc_feature
<222> LOCATION: (10)..(10)
<223> OTHER INFORMATION: n = uracil
<220> FEATURE:
<221> NAME/KEY: misc_feature
<222> LOCATION: (12)..(12)
<223> OTHER INFORMATION: n = uracil
<220> FEATURE:
<221> NAME/KEY: misc_feature
<222> LOCATION: (13)..(13)
<223> OTHER INFORMATION: n = uracil

<400> SEQUENCE: 13
gaagngacan cnncagcaat t                                               21

<210> SEQ ID NO 14
<211> LENGTH: 21
<212> TYPE: DNA
<213> ORGANISM: Artificial Sequence
<220> FEATURE:
<223> OTHER INFORMATION: Synthetic construct; siRNA antisense of com.2
```

```
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (1)..(1)
<223> OTHER INFORMATION: n = uracil
<220> FEATURE:
<221> NAME/KEY: misc_feature
<222> LOCATION: (2)..(2)
<223> OTHER INFORMATION: n = uracil
<220> FEATURE:
<221> NAME/KEY: misc_feature
<222> LOCATION: (5)..(5)
<223> OTHER INFORMATION: n = uracil
<220> FEATURE:
<221> NAME/KEY: misc_feature
<222> LOCATION: (11)..(11)
<223> OTHER INFORMATION: n = uracil
<220> FEATURE:
<221> NAME/KEY: misc_feature
<222> LOCATION: (13)..(13)
<223> OTHER INFORMATION: n = uracil
<220> FEATURE:
<221> NAME/KEY: misc_feature
<222> LOCATION: (17)..(17)
<223> OTHER INFORMATION: n = uracil
<220> FEATURE:
<221> NAME/KEY: misc_feature
<222> LOCATION: (18)..(18)
<223> OTHER INFORMATION: n = uracil

<400> SEQUENCE: 14
nngcngaaga ngncacnnct t                                              21

<210> SEQ ID NO 15
<211> LENGTH: 20
<212> TYPE: DNA
<213> ORGANISM: Artificial Sequence
<220> FEATURE:
<223> OTHER INFORMATION: Synthetic construct; IS for siRNA sense of
     exp.2
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (2)..(2)
<223> OTHER INFORMATION: n = uracil
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (4)..(4)
<223> OTHER INFORMATION: am
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: n = uracil
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (10)..(10)
<223> OTHER INFORMATION: am
<220> FEATURE:
<221> NAME/KEY: modified_base
```

```
<222> LOCATION: (12)..(12)
<223> OTHER INFORMATION: am
<220> FEATURE:
<221> NAME/KEY: misc_feature
<222> LOCATION: (13)..(13)
<223> OTHER INFORMATION: n = uracil
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (16)..(16)
<223> OTHER INFORMATION: cm
<220> FEATURE:
<221> NAME/KEY: misc_feature
<222> LOCATION: (17)..(17)
<223> OTHER INFORMATION: n = uracil
<220> FEATURE:
<221> NAME/KEY: modified_base
<222> LOCATION: (18)..(18)
<223> OTHER INFORMATION: gm

<400> SEQUENCE: 15
gngaagncaa cangccngct                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic construct; IS for siRNA antisense of
      exp.2
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (3)..(3)
<223> OTHER INFORMATION: am
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: am
<220> FEATURE:
<221> NAME/KEY: misc_feature
<222> LOCATION: (8)..(8)
<223> OTHER INFORMATION: n = uracil
<220> FEATURE:
<221> NAME/KEY: modified_base
<222> LOCATION: (9)..(9)
<223> OTHER INFORMATION: gm
<220> FEATURE:
<221> NAME/KEY: misc_feature
<222> LOCATION: (10)..(10)
<223> OTHER INFORMATION: n = uracil
<220> FEATURE:
<221> NAME/KEY: misc_feature
<222> LOCATION: (11)..(11)
<223> OTHER INFORMATION: n = uracil
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: am
```

```
<220> FEATURE:
<221> NAME/KEY: misc_feature
<222> LOCATION: (15)..(15)
<223> OTHER INFORMATION: n = uracil
<220> FEATURE:
<221> NAME/KEY: modified_base
<222> LOCATION: (15)..(15)
<223> OTHER INFORMATION: um
<220> FEATURE:
<221> NAME/KEY: misc_feature
<222> LOCATION: (16)..(16)
<223> OTHER INFORMATION: n = uracil
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (19)..(19)
<223> OTHER INFORMATION: cm

<400> SEQUENCE: 16
gcaggcangn ngacnncact                                                        20

<210> SEQ ID NO 17
<211> LENGTH: 20
<212> TYPE: DNA
<213> ORGANISM: Artificial Sequence
<220> FEATURE:
<223> OTHER INFORMATION: Synthetic construct; IS for siRNA sense of
      exp.3
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (2)..(2)
<223> OTHER INFORMATION: n = uracil
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (4)..(4)
<223> OTHER INFORMATION: am
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: n = uracil
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (10)..(10)
<223> OTHER INFORMATION: am
<220> FEATURE:
<221> NAME/KEY: modified_base
<222> LOCATION: (12)..(12)
<223> OTHER INFORMATION: am
<220> FEATURE:
<221> NAME/KEY: misc_feature
<222> LOCATION: (13)..(13)
<223> OTHER INFORMATION: n = uracil
<220> FEATURE:
<221> NAME/KEY: modified_base
<222> LOCATION: (14)..(14)
<223> OTHER INFORMATION: gm
<220> FEATURE:
<221> NAME/KEY: modified_base
```

```
<222> LOCATION: (16)..(16)
<223> OTHER INFORMATION: cm
<220> FEATURE:
<221> NAME/KEY: misc_feature
<222> LOCATION: (17)..(17)
<223> OTHER INFORMATION: n = uracil
<220> FEATURE:
<221> NAME/KEY: modified_base
<222> LOCATION: (18)..(18)
<223> OTHER INFORMATION: gm

<400> SEQUENCE: 17
gngaagncaa cangccngct                                                   20

<210> SEQ ID NO 18
<211> LENGTH: 20
<212> TYPE: DNA
<213> ORGANISM: Artificial Sequence
<220> FEATURE:
<223> OTHER INFORMATION: Synthetic construct; IS for siRNA antisense of
      exp.3
<220> FEATURE:
<221> NAME/KEY: misc_feature
<222> LOCATION: (1)..(18)
<223> OTHER INFORMATION: RNA
<220> FEATURE:
<221> NAME/KEY: misc_feature
<222> LOCATION: (7)..(7)
<223> OTHER INFORMATION: n = uracil
<220> FEATURE:
<221> NAME/KEY: misc_feature
<222> LOCATION: (9)..(9)
<223> OTHER INFORMATION: n = uracil
<220> FEATURE:
<221> NAME/KEY: misc_feature
<222> LOCATION: (10)..(10)
<223> OTHER INFORMATION: n = uracil
<220> FEATURE:
<221> NAME/KEY: misc_feature
<222> LOCATION: (14)..(14)
<223> OTHER INFORMATION: n = uracil
<220> FEATURE:
<221> NAME/KEY: misc_feature
<222> LOCATION: (15)..(15)
<223> OTHER INFORMATION: n = uracil

<400> SEQUENCE: 18
caggcangnn gacnncactt                                                   20

<210> SEQ ID NO 19
<211> LENGTH: 20
<212> TYPE: DNA
<213> ORGANISM: Artificial Sequence
<220> FEATURE:
<223> OTHER INFORMATION: Synthetic construct; IS for siRNA sense of
      com.2
<220> FEATURE:
<221> NAME/KEY: misc_feature
<222> LOCATION: (1)..(18)
<223> OTHER INFORMATION: RNA
<220> FEATURE:
<221> NAME/KEY: misc_feature
<222> LOCATION: (2)..(2)
<223> OTHER INFORMATION: n = uracil
<220> FEATURE:
<221> NAME/KEY: misc_feature
<222> LOCATION: (7)..(7)
<223> OTHER INFORMATION: n = uracil
<220> FEATURE:
<221> NAME/KEY: misc_feature
<222> LOCATION: (13)..(13)
<223> OTHER INFORMATION: n = uracil
<220> FEATURE:
<221> NAME/KEY: misc_feature
<222> LOCATION: (17)..(17)
```

<223> OTHER INFORMATION: n = uracil

<400> SEQUENCE: 19
gngaagncaa cangccngtt                                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic construct; IS for siRNA antisense of
      com.2
<220> FEATURE:
<221> NAME/KEY: misc_feature
<222> LOCATION: (1)..(18)
<223> OTHER INFORMATION: RNA
<220> FEATURE:
<221> NAME/KEY: misc_feature
<222> LOCATION: (7)..(7)
<223> OTHER INFORMATION: n = uracil
<220> FEATURE:
<221> NAME/KEY: misc_feature
<222> LOCATION: (9)..(9)
<223> OTHER INFORMATION: n = uracil
<220> FEATURE:
<221> NAME/KEY: misc_feature
<222> LOCATION: (10)..(10)
<223> OTHER INFORMATION: n = uracil
<220> FEATURE:
<221> NAME/KEY: misc_feature
<222> LOCATION: (14)..(14)
<223> OTHER INFORMATION: n = uracil
<220> FEATURE:
<221> NAME/KEY: misc_feature
<222> LOCATION: (15)..(15)
<223> OTHER INFORMATION: n = uracil

<400> SEQUENCE: 20
caggcangnn gacnncactt                                                    20

<210> SEQ ID NO 21
<211> LENGTH: 25
<212> TYPE: DNA
<213> ORGANISM: Artificial Sequence
<220> FEATURE:
<223> OTHER INFORMATION: Synthetic construct; siRNA sense of exp.4
<220> FEATURE:
<221> NAME/KEY: misc_feature
<222> LOCATION: (1)..(23)
<223> OTHER INFORMATION: RNA
<220> FEATURE:
<221> NAME/KEY: modified_base
<222> LOCATION: (2)..(2)
<223> OTHER INFORMATION: am
<220> FEATURE:
<221> NAME/KEY: modified_base
<222> LOCATION: (4)..(4)
<223> OTHER INFORMATION: gm
<220> FEATURE:
<221> NAME/KEY: misc_feature
<222> LOCATION: (5)..(5)
<223> OTHER INFORMATION: n = uracil
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (8)..(8)
<223> OTHER INFORMATION: cm
<220> FEATURE:
<221> NAME/KEY: misc_feature
<222> LOCATION: (10)..(10)
<223> OTHER INFORMATION: n = uracil
<220> FEATURE:

```
<221> NAME/KEY: modified_base
<222> LOCATION: (10)..(10)
<223> OTHER INFORMATION: um
<220> FEATURE:
<221> NAME/KEY: misc_feature
<222> LOCATION: (12)..(12)
<223> OTHER INFORMATION: n = uracil
<220> FEATURE:
<221> NAME/KEY: modified_base
<222> LOCATION: (12)..(12)
<223> OTHER INFORMATION: um
<220> FEATURE:
<221> NAME/KEY: misc_feature
<222> LOCATION: (13)..(13)
<223> OTHER INFORMATION: n = uracil
<220> FEATURE:
<221> NAME/KEY: modified_base
<222> LOCATION: (14)..(14)
<223> OTHER INFORMATION: cm
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (18)..(18)
<223> OTHER INFORMATION: am
<220> FEATURE:
<221> NAME/KEY: modified_base
<222> LOCATION: (20)..(20)
<223> OTHER INFORMATION: am
<220> FEATURE:
<221> NAME/KEY: misc_feature
<222> LOCATION: (21)..(21)
<223> OTHER INFORMATION: n = uracil
<220> FEATURE:
<221> NAME/KEY: modified_base
<222> LOCATION: (22)..(22)
<223> OTHER INFORMATION: am

<400> SEQUENCE: 21
gaagngacan cnncagcaaa naaac                                            25

<210> SEQ ID NO 22
<211> LENGTH: 27
<212> TYPE: RNA
<213> ORGANISM: Artificial Sequence
<220> FEATURE:
<223> OTHER INFORMATION: Synthetic construct; siRNA antisense of exp.4
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (5)..(5)
<223> OTHER INFORMATION: am
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (9)..(9)
<223> OTHER INFORMATION: gm
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: am
<220> FEATURE:
<221> NAME/KEY: modified_base
<222> LOCATION: (15)..(15)
<223> OTHER INFORMATION: gm
```

```
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (21)..(21)
<223> OTHER INFORMATION: am
<220> FEATURE:
<221> NAME/KEY: modified_base
<222> LOCATION: (23)..(23)
<223> OTHER INFORMATION: um
<220> FEATURE:
<221> NAME/KEY: modified_base
<222> LOCATION: (25)..(25)
<223> OTHER INFORMATION: cm
<220> FEATURE:
<221> NAME/KEY: modified_base
<222> LOCATION: (26)..(26)
<223> OTHER INFORMATION: um
<220> FEATURE:
<221> NAME/KEY: modified_base
<222> LOCATION: (27)..(27)
<223> OTHER INFORMATION: um

<400> SEQUENCE: 22
guuuauuugc ugaagauguc acuucuu                                       27

<210> SEQ ID NO 23
<211> LENGTH: 25
<212> TYPE: DNA
<213> ORGANISM: Artificial Sequence
<220> FEATURE:
<223> OTHER INFORMATION: Synthetic construct; siRNA sense of com.3
<220> FEATURE:
<221> NAME/KEY: misc_feature
<222> LOCATION: (1)..(23)
<223> OTHER INFORMATION: RNA
<220> FEATURE:
<221> NAME/KEY: misc_feature
<222> LOCATION: (5)..(5)
<223> OTHER INFORMATION: n = uracil
<220> FEATURE:
<221> NAME/KEY: misc_feature
<222> LOCATION: (10)..(10)
<223> OTHER INFORMATION: n = uracil
<220> FEATURE:
<221> NAME/KEY: misc_feature
<222> LOCATION: (12)..(12)
<223> OTHER INFORMATION: n = uracil
<220> FEATURE:
<221> NAME/KEY: misc_feature
<222> LOCATION: (13)..(13)
<223> OTHER INFORMATION: n = uracil
<220> FEATURE:
<221> NAME/KEY: misc_feature
<222> LOCATION: (21)..(21)
<223> OTHER INFORMATION: n = uracil

<400> SEQUENCE: 23
gaagngacan cnncagcaaa naaac                                         25

<210> SEQ ID NO 24
<211> LENGTH: 27
<212> TYPE: RNA
<213> ORGANISM: Artificial Sequence
<220> FEATURE:
<223> OTHER INFORMATION: Synthetic construct; siRNA antisense of com.4

<400> SEQUENCE: 24
```
guuuauuugc ugaagauguc acuucuu                                    27

<210> SEQ ID NO 25
<211> LENGTH: 20
<212> TYPE: DNA
<213> ORGANISM: Artificial Sequence
<220> FEATURE:
<223> OTHER INFORMATION: Synthetic construct; IS for siRNA sense of
      exp.4
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (2)..(2)
<223> OTHER INFORMATION: n = uracil
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (4)..(4)
<223> OTHER INFORMATION: am
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: n = uracil
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (10)..(10)
<223> OTHER INFORMATION: am
<220> FEATURE:
<221> NAME/KEY: modified_base
<222> LOCATION: (12)..(12)
<223> OTHER INFORMATION: am
<220> FEATURE:
<221> NAME/KEY: misc_feature
<222> LOCATION: (13)..(13)
<223> OTHER INFORMATION: n = uracil
<220> FEATURE:
<221> NAME/KEY: modified_base
<222> LOCATION: (14)..(14)
<223> OTHER INFORMATION: gm
<220> FEATURE:
<221> NAME/KEY: modified_base
<222> LOCATION: (16)..(16)
<223> OTHER INFORMATION: cm
<220> FEATURE:
<221> NAME/KEY: misc_feature
<222> LOCATION: (17)..(17)
<223> OTHER INFORMATION: n = uracil
<220> FEATURE:
<221> NAME/KEY: modified_base
<222> LOCATION: (18)..(18)
<223> OTHER INFORMATION: gm

<400> SEQUENCE: 25
gngaagncaa cangccngct                                            20

<210> SEQ ID NO 26
<211> LENGTH: 20
<212> TYPE: DNA
<213> ORGANISM: Artificial Sequence
<220> FEATURE:
<223> OTHER INFORMATION: Synthetic construct; IS for siRNA antisense of
      exp.4

```
<220> FEATURE:
<221> NAME/KEY: misc_feature
<222> LOCATION: (1)..(19)
<223> OTHER INFORMATION: RNA
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (3)..(3)
<223> OTHER INFORMATION: am
<220> FEATURE:
<221> NAME/KEY: modified_base
<222> LOCATION: (5)..(5)
<223> OTHER INFORMATION: gm
<220> FEATURE:
<221> NAME/KEY: modified_base
<222> LOCATION: (7)..(7)
<223> OTHER INFORMATION: am
<220> FEATURE:
<221> NAME/KEY: misc_feature
<222> LOCATION: (8)..(8)
<223> OTHER INFORMATION: n = uracil
<220> FEATURE:
<221> NAME/KEY: modified_base
<222> LOCATION: (9)..(9)
<223> OTHER INFORMATION: gm
<220> FEATURE:
<221> NAME/KEY: misc_feature
<222> LOCATION: (10)..(10)
<223> OTHER INFORMATION: n = uracil
<220> FEATURE:
<221> NAME/KEY: misc_feature
<222> LOCATION: (11)..(11)
<223> OTHER INFORMATION: n = uracil
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (13)..(13)
<223> OTHER INFORMATION: am
<220> FEATURE:
<221> NAME/KEY: misc_feature
<222> LOCATION: (15)..(15)
<223> OTHER INFORMATION: n = uracil
<220> FEATURE:
<221> NAME/KEY: modified_base
<222> LOCATION: (15)..(15)
<223> OTHER INFORMATION: um
<220> FEATURE:
<221> NAME/KEY: misc_feature
<222> LOCATION: (16)..(16)
<223> OTHER INFORMATION: n = uracil
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (19)..(19)
<223> OTHER INFORMATION: cm

<400> SEQUENCE: 26
gcaggcangn ngacnncact                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic construct; IS for siRNA sense of
      com.3
<220> FEATURE:
<221> NAME/KEY: misc_feature
```

```
<222> LOCATION: (1)..(18)
<223> OTHER INFORMATION: RNA
<220> FEATURE:
<221> NAME/KEY: misc_feature
<222> LOCATION: (2)..(2)
<223> OTHER INFORMATION: n = uracil
<220> FEATURE:
<221> NAME/KEY: misc_feature
<222> LOCATION: (7)..(7)
<223> OTHER INFORMATION: n = uracil
<220> FEATURE:
<221> NAME/KEY: misc_feature
<222> LOCATION: (13)..(13)
<223> OTHER INFORMATION: n = uracil
<220> FEATURE:
<221> NAME/KEY: misc_feature
<222> LOCATION: (17)..(17)
<223> OTHER INFORMATION: n = uracil

<400> SEQUENCE: 27
gngaagncaa cangccngtt                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic construct; IS for siRNA antisense of
      com.3
<220> FEATURE:
<221> NAME/KEY: misc_feature
<222> LOCATION: (1)..(18)
<223> OTHER INFORMATION: RNA
<220> FEATURE:
<221> NAME/KEY: misc_feature
<222> LOCATION: (7)..(7)
<223> OTHER INFORMATION: n = uracil
<220> FEATURE:
<221> NAME/KEY: misc_feature
<222> LOCATION: (9)..(9)
<223> OTHER INFORMATION: n = uracil
<220> FEATURE:
<221> NAME/KEY: misc_feature
<222> LOCATION: (10)..(10)
<223> OTHER INFORMATION: n = uracil
<220> FEATURE:
<221> NAME/KEY: misc_feature
<222> LOCATION: (14)..(14)
<223> OTHER INFORMATION: n = uracil
<220> FEATURE:
<221> NAME/KEY: misc_feature
<222> LOCATION: (15)..(15)
<223> OTHER INFORMATION: n = uracil

<400> SEQUENCE: 28
caggcangnn gacnncactt                                              20

<210> SEQ ID NO 29
<211> LENGTH: 6492
<212> TYPE: DNA
<213> ORGANISM: Homo sapiens
<220> FEATURE:
<221> NAME/KEY: misc_feature
<223> OTHER INFORMATION: bcl2 mRNA

<400> SEQUENCE: 29
tttctgtgaa gcagaagtct gggaatcgat ctggaaatcc tcctaatttt tactccctct     60
ccccgcgact cctgattcat tgggaagttt caaatcagct ataactggag agtgctgaag    120
attgatggga tcgttgcctt atgcatttgt tttggtttta caaaaaggaa acttgacaga    180
ggatcatgct gtacttaaaa aatacaacat cacagaggaa gtagactgat attaacaata    240
```

```
cttactaata ataacgtgcc tcatgaaata aagatccgaa aggaattgga ataaaaattt      300
cctgcatctc atgccaaggg ggaaacacca gaatcaagtg ttccgcgtga ttgaagacac      360
cccctcgtcc aagaatgcaa agcacatcca ataaaatagc tggattataa ctcctcttct      420
ttctctgggg gccgtgtgggt gggagctggg gcgagaggtg ccgttggccc ccgttgcttt      480
tcctctggga aggatggcgc acgctgggag aacagggtac gataaccggg agatagtgat      540
gaagtacatc cattataagc tgtcgcagag gggctacgag tgggatgcgg gagatgtggg      600
cgccgcgccc ccgggggccg cccccgcacc gggcatcttc tcctcccagc ccgggcacac      660
gccccatcca gccgcatccc gggacccggt cgccaggacc tcgccgctgc agacccggc       720 tgccccggc gccgccgcgg ggcctgcgct cagcccggtg ccacctgtgg tccacctgac       780
cctccgccag gccggcgacg acttctcccg ccgctaccgc cgcgacttcg ccgagatgtc      840
cagccagctg cacctgacgc ccttcaccgc gcggggacgc tttgccacgg tggtggagga      900
gctcttcagg gacggggtga actgggggag gattgtggcc ttctttgagt tcggtggggt      960
catgtgtgtg gagagcgtca accgggagat gtcgcccctg gtggacaaca tcgccctgtg     1020
gatgactgag tacctgaacc ggcacctgca cacctggatc caggataacg gaggctggga     1080
tgcctttgtg gaactgtacg gccccagcat gcggcctctg tttgatttct cctggctgtc     1140
tctgaagact ctgctcagtt tggccctggt gggagcttgc atcaccctgg gtgcctatct     1200
gggccacaag tgaagtcaac atgcctgccc caaacaaata tgcaaaaggt tcactaaagc     1260
agtagaaata atatgcattg tcagtgatgt accatgaaac aaagctgcag gctgtttaag     1320
aaaaaataac acacatataa acatcacaca cacagacaga cacacacaca cacaacaatt     1380
aacagtcttc aggcaaaacg tcgaatcagc tatttactgc caaagggaaa tatcatttat     1440 ttttacatt attaagaaaa aaagatttat ttatttaaga cagtcccatc aaaactcctg     1500
tctttggaaa tccgaccact aattgccaag caccgcttcg tgtggctcca cctggatgtt     1560
ctgtgcctgt aaacatagat tcgctttcca tgttgttggc cggatcacca tctgaagagc     1620
agacggatgg aaaaaggacc tgatcattgg ggaagctggc tttctggctg ctggaggctg     1680
gggagaaggt gttcattcac ttgcatttct ttgccctggg ggctgtgata ttaacagagg     1740
gagggttcct gtgggggaa gtccatgcct ccctggcctg aagaagagac tctttgcata     1800
tgactcacat gatgcatacc tggtgggagg aaaagagttg ggaacttcag atggacctag     1860
tacccactga gatttccacg ccgaaggaca gcgatgggaa aaatgccctt aaatcatagg     1920
aaagtatttt tttaagctac caattgtgcc gagaaaagca ttttagcaat ttatacaata     1980
tcatccagta ccttaagccc tgattgtgta tattcatata ttttggatac gcaccccca      2040 actcccaata ctggctctgt ctgagtaaga aacagaatcc tctggaactt gaggaagtga     2100
acatttcggt gacttccgca tcaggaaggc tagagttacc cagagcatca ggccgccaca     2160
agtgcctgct tttaggagac cgaagtccgc agaacctgcc tgtgtcccag cttggaggcc     2220
tggtcctgga actgagccgg ggccctcact ggcctcctcc agggatgatc aacagggcag     2280
tgtggtctcc gaatgtctgg aagctgatgg agctcagaat tccactgtca agaaagagca     2340
gtagaggggt gtggctgggc ctgtcaccct gggccctcc aggtaggccc gttttcacgt      2400
ggagcatggg agccacgacc cttcttaaga catgtatcac tgtagaggga aggaacagag     2460
gccctgggcc cttcctatca gaaggacatg gtgaaggctg ggaacgtgag gagaggcaat     2520
ggccacggcc cattttggct gtagcacatg gcacgttggc tgtgtggcct ggcccacct      2580 gtgagtttaa agcaaggctt taaatgactt tggagagggt cacaaatcct aaaagaagca     2640
```

```
ttgaagtgag gtgtcatgga ttaattgacc cctgtctatg gaattacatg taaaacatta    2700
tcttgtcact gtagtttggt tttatttgaa aacctgacaa aaaaaaagtt ccaggtgtgg    2760
aatatggggg ttatctgtac atcctggggc attaaaaaaa aaatcaatgg tggggaacta    2820
taaagaagta acaaaagaag tgacatcttc agcaaataaa ctaggaaatt ttttttttctt   2880
ccagtttaga atcagccttg aaacattgat ggataactc tgtggcatta ttgcattata     2940
taccatttat ctgtattaac tttggaatgt actctgttca atgttaatg ctgtggttga     3000
tatttcgaaa gctgctttaa aaaatacat gcatctcagc gttttttgt tttaattgt       3060
atttagttat ggcctataca ctatttgtga gcaaggtga tcgttttctg tttgagattt     3120
ttatctcttg attcttcaaa agcattctga aaggtgaga taagccctga gtctcagcta    3180
cctaagaaaa acctggatgt cactggccac tgaggagctt tgtttcaacc aagtcatgtg   3240
catttccacg tcaacagaat tgtttattgt gacagttata tctgttgtcc ctttgacctt   3300
gtttcttgaa ggtttcctcg tccctgggca attccgcatt taattcatgg tattcaggat   3360
tacatgcatg tttggttaaa cccatgagat tcattcagtt aaaaatccag atggcaaatg   3420
accagcagat tcaaatctat ggtggtttga cctttagaga gttgctttac gtggcctgtt   3480
tcaacacaga cccacccaga gccctcctgc cctccttccg cggggggcttt ctcatggctg   3540
tccttcaggg tcttcctgaa atgcagtggt gcttacgctc caccaagaaa gcaggaaacc   3600
tgtggtatga agccagacct ccccggcggg cctcagggaa cagaatgatc agacctttga   3660
atgattctaa tttttaagca aaatattatt ttatgaaagg tttacattgt caaagtgatg   3720
aatatggaat atccaatcct gtgctgctat cctgccaaaa tcattttaat ggagtcagtt    3780
tgcagtatgc tccacgtggt aagatcctcc aagctgcttt agaagtaaca atgaagaacg   3840
tggacgtttt taatataaag cctgtttttgt cttttgttgt tgttcaaacg ggattcacag   3900
agtatttgaa aaatgtatat atattaagag gtcacggggg ctaattgctg gctggctgcc    3960
ttttgctgtg gggttttgtt acctggtttt aataacagta aatgtgccca gcctcttggc   4020
cccagaactg tacagtattg tggctgcact tgctctaaga gtagttgatg ttgcattttc   4080
cttattgtta aaaacatgtt agaagcaatg aatgtatata aaagcctcaa ctagtcattt   4140
ttttctcctc ttcttttttt tcattatatc taattatttt gcagttgggc aacagagaac   4200
catcccctatt ttgtattgaa gagggattca catctgcatc ttaactgctc tttatgaatg   4260
aaaaaacagt cctctgtatg tactcctctt tacactggcc agggtcagag ttaaatagag   4320
tatatgcact ttccaaattg gggacaaggg ctctaaaaaa agccccaaaa ggagaagaac   4380
atctgagaac ctcctcggcc ctcccagtcc ctcgctgcac aaatactccg caagagaggc   4440
cagaatgaca gctgacaggg tctatggcca tcgggtcgtc tccgaagatt tggcagggggc  4500
agaaaactct ggcaggctta agatttggaa taaagtcaca gaattaagga agcacctcaa   4560
tttagttcaa acaagacgcc aacattctct ccacagctca cttacctctc tgtgttcaga   4620
tgtggccttc catttatatg tgatctttgt tttattagta aatgcttatc atctaaagat   4680
gtagctctgg cccagtggga aaaattagga agtgattata atcgagagg agttataata    4740
atcaagatta aatgtaaata atcagggcaa tcccaacaca tgtctagctt tcacctccag   4800
gatctattga gtgaacagaa ttgcaaatag tctctatttg taattgaact tatcctaaaa   4860
caaatagttt ataaatgtga acttaaactc taattaattc caactgtact tttaaggcag   4920
tggctgtttt tagactttct tatcacttat agttagtaat gtacacctac tctatcagag   4980
```

```
aaaaacagga aaggctcgaa atacaagcca ttctaaggaa attagggagt cagttgaaat    5040
tctattctga tcttattctg tggtgtcttt tgcagcccag acaaatgtgg ttacacactt    5100
tttaagaaat acaattctac attgtcaagc ttatgaaggt tccaatcaga tctttattgt    5160
tattcaattt ggatctttca gggattttt ttttaaatta ttatgggaca aaggacattt     5220
gttggagggg tgggagggag gaagaatttt taaatgtaaa acattcccaa gtttggatca    5280
gggagttgga agttttcaga ataaccagaa ctaagggtat gaaggacctg tattggggtc    5340
gatgtgatgc ctctgcgaag aaccttgtgt gacaaatgag aaacattttg aagtttgtgg    5400
tacgaccttt agattccaga gacatcagca tggctcaaag tgcagctccg tttggcagtg    5460
caatggtata aatttcaagc tggatatgtc taatgggtat ttaaacaata aatgtgcagt    5520
tttaactaac aggatattta atgacaacct tctggttggt agggacatct gtttctaaat    5580
gtttattatg tacaatacag aaaaaaattt tataaaatta agcaatgtga aactgaattg    5640
gagagtgata atacaagtcc tttagtctta cccagtgaat cattctgttc catgtctttg    5700
gacaaccatg accttggaca atcatgaaat atgcatctca ctggatgcaa agaaaatcag    5760
atggagcatg aatggtactg taccggttca tctggactgc cccagaaaaa taacttcaag    5820
caaacatcct atcaacaaca aggttgttct gcataccaag ctgagcacag aagatgggaa    5880
cactggtgga ggatggaaag gctcgctcaa tcaagaaaat tctgagacta ttaataaata    5940
agactgtagt gtagatactg agtaaatcca tgcacctaaa cctttgggaa aatctgccgt    6000
gggccctcca gatagctcat ttcattaagt ttttccctcc aaggtagaat ttgcaagagt    6060
gacagtggat tgcatttctt ttggggaagc tttcttttgg tggttttgtt tattatacct    6120
tcttaagttt tcaaccaagg tttgcttttg ttttgagtta ctggggttat ttttgtttta    6180
aataaaaata agtgtacaat aagtgttttt gtattgaaag cttttgttat caagattttc    6240
atacttttac cttccatggc tcttttaag attgatactt ttaagaggtg gctgatattc     6300
tgcaacactg tacacataaa aaatacggta aggatacttt acatggttaa ggtaaagtaa    6360
gtctccagtt ggccaccatt agctataatg gcactttgtt tgtgttgttg gaaaaagtca    6420
cattgccatt aaactttcct tgtctgtcta gttaatattg tgaagaaaaa taaagtacag    6480
tgtgagatac tg                                                        6492
```

COMPOSITION FOR SUPPRESSING EXPRESSION OF TARGET GENE

This application is a CIP of International PCT Application No. PCT/JP2009/063685 filed Jul. 31, 2009.

TECHNICAL FIELD

The present invention relates to a composition for suppressing the expression of a target gene, and the like.

BACKGROUND ART

As a method of suppressing the expression of a target gene, for example, a method utilizing RNA interference (hereinafter referred to as RNAi) and the like are known, and specifically, a phenomenon in which when a double-stranded RNA having a sequence identical to that of a target gene is introduced into Nematoda, the expression of the target gene is specifically suppressed has been reported (see "Nature", Vol. 391, No. 6669, pp. 806-811, 1998). Further, it has been found that even when a double-stranded RNA having a length of 21 to 23 bases is introduced into Drosophila, instead of a long double-stranded RNA, the expression of a target gene is suppressed. This is named short interfering RNA (siRNA) (see International Publication No. WO 01/75164).

In the case of mammalian cells, when a long double-stranded RNA was introduced, apoptosis took place as a result of the functions of virus defense mechanism, and thus the expression of a specific gene could not be suppressed. However, it has been found that when siRNA having a length of 20 to 29 bases is used, such a reaction does not take place, and that the expression of a specific gene can be suppressed. Among others, siRNA having 21 to 25 bases has a high effect of suppressing expression ("Nature", Vol. 411, No. 6836, pp. 494-498, 2001; "Nature Reviews Genetics", Vol. 3, No. 10, pp. 737-747, 2002; "Molecular Cell", (USA) Vol. 10, No. 3, pp. 549-561, 2002; "Nature Biotechnology", (USA) Vol. 20, No. 5, pp. 497-500, 2002). In addition, it has also been reported that not only a double-stranded RNA, but also a single-stranded RNA having a hairpin structure as a result of intramolecular hybridization, exhibits RNAi, as with siRNA (see "Proceedings of the National Academy of Sciences of the United States of America", Vol. 99, No. 9, pp. 6047-6052, 2002).

RNAi has been frequently verified in also in vivo tests. The effect of RNAi using siRNA with a length of 50 base pairs or less on fetal animals (see Patent document 1) and the effect thereof on adult mice (see Patent document 2) have been reported. Moreover, when siRNA is intravenously administered to a fetal mouse, the effect of suppressing the expression of a specific gene has been found in various organs such as kidney, spleen, lung, pancreas, and liver (see Non-patent document 1). Furthermore, it has been reported that when siRNA is directly administered to brain cells, the expression of a specific gene is also suppressed (see Non-patent document 2).

On the other hand, as means for delivering a nucleic acid into a cell, a method using cationic lipid particle or cationic polymers is known. However, by the method, after intravenous administration of cationic lipid particle or cationic polymers containing a nucleic acid is carried out, the nucleic acid is promptly removed from the blood, and when a target tissue is different from liver or lung, for example, when it is a tumor site or the like, the nucleic acid cannot be delivered to the target tissue, and therefore, the expression of a sufficient action has not been made possible yet. Accordingly, a nucleic acid-encapsulating lipid particle (lipid particle encapsulating a nucleic acid therein) with which the problem that a nucleic acid is promptly removed from the blood was solved has been reported (see Patent documents 3 to 6, and Non-patent document 3). In the Patent document 3, as a method of producing lipid particle encapsulating a nucleic acid or the like, for example, a method of producing an oligodeoxynucleotide (ODN)-encapsulating lipid particle by dissolving a cationic lipid in chloroform in advance, adding an aqueous solution of ODN and methanol thereto and mixing and centrifuging the mixture thereby transferring a complex of the cationic lipid and ODN to a chloroform layer, and then taking out the chloroform layer, adding a polyethylene glycolated phospholipid, a neutral lipid, and water to the chloroform layer to form a water-in-oil (w/o) emulsion and treating the emulsion by the reverse phase evaporation method has been reported. In Patent document 4 and Non-patent document 3, a method of producing an ODN-encapsulating lipid particle by dissolving ODN in an aqueous solution of citric acid at pH 3.8, adding a lipid (in ethanol) to the solution, reducing the ethanol concentration to 20 v/v % to prepare an ODN-encapsulating lipid particle, performing filtration for sizing, removing excess ethanol by dialysis, and then further performing dialysis of the sample at pH 7.5 to remove ODN adhering to the surface of the lipid particle has been reported. In each method, a lipid particle encapsulating an active ingredient such as a nucleic acid is produced.

On the other hand, in Patent documents 5 and 6, it has been reported that a lipid particle encapsulating an active ingredient such as a nucleic acid is produced by a method of coating fine particles with a lipid bilayer membrane in a liquid. In the method, fine particles are coated with a lipid bilayer membrane in liquid by reducing the concentration of the polar organic solvent in a polar organic solvent-containing aqueous solution in which the fine particles are dispersed and a lipid is dissolved. In the method, for example, fine particles coated with a lipid bilayer membrane (coated fine particles) having a size suitable for fine particles for intravenous injection and the like are produced very efficiently. In addition, as an example of the fine particles to be coated, for example, a complex which consists of ODN or siRNA and a cationic lipid and is formed by an electrostatic interaction is exemplified in Patent documents 5 and 6. It has been reported that the particle diameter of the coated fine particles obtained by coating the fine particles is small and is suitable for using as an injection, and the coated fine particles show high retention in the blood and are much accumulated in a tumor tissue when they are intravenously administered.

Patent document 1: United States Publication No. US 2002-132788
Patent document 2: International Publication No. WO 03/10180
Patent document 3: Published Japanese translation of a PCT international application No. 2002-508765
Patent document 4: Published Japanese translation of a PCT international application No. 2002-501511
Patent document 5: International Publication No. WO 02/28367
Patent document 6: International Publication No. WO 2006/080118
Non-patent document 1: "Nature Genetics", Vol. 32, No. 1, pp. 107-108, 2002
Non-patent document 2: "Nature Biotechnology", Vol. 20, No. 10, pp. 1006-1010, 2002

Non-patent document 3: "Biochimica et Biophysica Acta", Vol. 1510, pp. 152-166, 2001

SUMMARY OF THE INVENTION

Problems to be Solved by the Invention

An object of the present invention is to provide a composition for suppressing expression of a target gene, and the like.

Means for Solving the Problems

The present invention relates to the following (1) to (54).

(1) A composition comprising an RNA-encapsulated lipid particle, wherein the RNA contains a sequence consisting of 15 to 30 contiguous bases of a target gene mRNA (hereinafter, sequence X) and a base sequence (hereinafter, complementary sequence X') complementary to the sequence X, 1 to 90% of all sugars binding to the bases of the sequence X and the complementary sequence X' being ribose substituted by a modifying group at 2' position, and the lipid particle_being capable of reaching a tissue or an organ containing an expression site of the target gene.

(2) The composition according to the above (1), wherein the lipid particle is a lipid particle having a size that allows intravenous administration.

(3) The composition according to the above (1) or (2), wherein the RNA is an RNA having an action of suppressing the expression of the target gene by utilizing RNA interference (RNAi).

(4) The composition according to any one of the above (1) to (3), wherein the target gene is a gene associated with tumor or inflammation.

(5) The composition according to any one of the above (1) to (4), wherein the target gene is a gene associated with angiogenesis.

(6) The composition according to any one of the above (1) to (4), wherein the target gene is a gene of any one of a vascular endothelial growth factor, a vascular endothelial growth factor receptor, a fibroblast growth factor, a fibroblast growth factor receptor, a platelet-derived growth factor, a platelet-derived growth factor receptor, a hepatocyte growth factor, a hepatocyte growth factor receptor, a Krüppel-like factor, an Ets transcription factor, a nuclear factor, and a hypoxia-inducible factor.

(7) The composition according to any one of the above (1) to (6), wherein the mRNA is either human mRNA or mouse mRNA.

(8) The composition according to any one of the above (1) to (7), wherein the RNA-encapsulated lipid particle includes:
a complex particle that contains a lead particle, in other words the primary leading particle of this invention, and the RNA as constituent components; and
a lipid bilayer membrane for coating the complex particle,
wherein constituent components of the lipid bilayer membrane are soluble in a polar organic solvent, and wherein the constituent components of the lipid bilayer membrane, and the complex particle are dispersible in a liquid that contains the polar organic solvent in a specific concentration.

(9) The composition according to the above (8), wherein the polar organic solvent is an alcohol.

(10) The composition according to the above (8), wherein the polar organic solvent is ethanol.

(11) The composition according to any one of the above (8) to (10), wherein the lead particle contains a cationic substance, and wherein the lipid bilayer membrane contains, as constituent components, a neutral lipid, and a lipid derivative, a fatty acid derivative, or an aliphatic hydrocarbon derivative of a water-soluble substance.

(12) The composition according to any one of the above (1) to (7), wherein the RNA-encapsulated lipid particle is a lipid particle that includes: a complex particle that contains a cationic substance-containing lead particle and the RNA as constituent components; and a lipid bilayer membrane for coating the complex particle,
wherein the lipid bilayer membrane contains, as constituent components, a neutral lipid, and a lipid derivative, a fatty acid derivative, or an aliphatic hydrocarbon derivative of a water-soluble substance.

(13) The composition according to the above (11) or (12), wherein the cationic substance is one or more compounds selected from N-[1-(2,3-dioleoylpropyl)]-N,N,N-trimethylammonium chloride, N-[1-(2,3-dioleoylpropyl)]-N,N-dimethylamine, N-[1-(2,3-dioleyloxypropyl)-N,N,N-trimethylammonium chloride, N-[1-(2,3-ditetradecyloxypropyl)]-N,N-dimethyl-N-hydroxyethylammonium bromide, and 3β-[N—(N',N'-dimethylaminoethyl)carbamoyl]cholesterol.

(14) The composition according to any one of the above (11) to (13), wherein the lipid derivative, the fatty acid derivative, or the aliphatic hydrocarbon derivative of a water-soluble substance is polyethylene glycol phosphatidyl ethanolamine.

(15) The composition according to any one of the above (11) to (14), wherein the neutral lipid is egg yolk phosphatidylcholine.

(16) A method for improving blood RNA concentration when a composition comprising an RNA-encapsulated lipid particle is second administered to a mammal, which comprises selecting the RNA contains a sequence consisting of 15 to 30 contiguous bases of a target gene mRNA (hereinafter, sequence X) and a base sequence (hereinafter, complementary sequence X') complementary to the sequence X, and substituting the some of ribose binding to the bases of the sequence X and/or the complementary sequence X' by a modifying group at 2' position,
wherein 1 to 90% of all sugars binding to the bases of the sequence X and the complementary sequence X' are ribose substituted by a modifying group at 2' position.

(17) The method according to the above (16), wherein the lipid particle is a lipid particle having a size that allows intravenous administration.

(18) The method according to the above (16) or (17), wherein the RNA is an RNA having an action of suppressing the expression of the target gene by utilizing RNA interference (RNAi).

(19) The method according to any one of the above (16) to (18), wherein the target gene is a gene associated with tumor or inflammation.

(20) The method according to any one of the above (16) to (19), wherein the target gene is a gene associated with angiogenesis.

(21) The method according to any one of the above (16) to (19), wherein the target gene is a gene of any one of a vascular endothelial growth factor, a vascular endothelial growth factor receptor, a fibroblast growth factor, a fibroblast growth factor receptor, a platelet-derived growth factor, a platelet-derived growth factor receptor, a hepatocyte growth factor, a hepatocyte growth factor receptor, a Krüppel-like factor, an Ets transcription factor, a nuclear factor, and a hypoxia-inducible factor.

(22) The method according to any one of the above (16) to (21), wherein the mRNA is either human mRNA or mouse mRNA.

(23) The method according to any one of the above (16) to (22), wherein the RNA-encapsulated lipid particle comprises:
a complex particle that contains a lead particle and the RNA as constituent components; and
a lipid bilayer membrane for coating the complex particle,
wherein constituent components of the lipid bilayer membrane are soluble in a polar organic solvent, and wherein the constituent components of the lipid bilayer membrane, and the complex particle are dispersible in a liquid that contains the polar organic solvent in a specific concentration.

(24) The method according to the above (23), wherein the polar organic solvent is an alcohol.

(25) The method according to the above (23), wherein the polar organic solvent is ethanol.

(26) The method according to any one of the above (23) to (25), wherein the lead particle contains a cationic substance, and wherein the lipid bilayer membrane contains, as constituent components, a neutral lipid, and a lipid derivative, a fatty acid derivative, or an aliphatic hydrocarbon derivative of a water-soluble substance.

(27) The method according to any one of the above (16) to (22), wherein the RNA-encapsulated lipid particle is a lipid particle that comprises: a complex particle that contains a cationic substance-containing lead particle and the RNA as constituent components; and a lipid bilayer membrane for coating the complex particle,
wherein the lipid bilayer membrane contains, as constituent components, a neutral lipid, and a lipid derivative, a fatty acid derivative, or an aliphatic hydrocarbon derivative of a water-soluble substance.

(28) The method according to the above (26) or (27), wherein the cationic substance is one or more compounds selected from N-[1-(2,3-dioleoylpropyl)]-N,N,N-trimethylammonium chloride, N-[1-(2,3-dioleoylpropyl)]-N,N-dimethylamine, N-[1-(2,3-dioleyloxypropyl)-N,N,N-trimethylammonium chloride, N-[1-(2,3-ditetradecyloxypropyl)]-N,N-dimethyl-N-hydroxyethylammonium bromide, and 3β-[N—(N',N'-dimethylaminoethyl)carbamoyl]cholesterol.

(29) The method according to any one of the above (26) to (28), wherein the lipid derivative, the fatty acid derivative, or the aliphatic hydrocarbon derivative of a water-soluble substance is polyethylene glycol phosphatidyl ethanolamine.

(30) The method according to any one of the above (26) to (29), wherein the neutral lipid is egg yolk phosphatidylcholine.

(31) A method for treating cancer or inflammatory disease, which comprises administering to a mammal a composition that comprises a lipid particle that includes:
a complex particle that contains, as constituent components, a lead particle, and an RNA that contains a sequence consisting of 15 to 30 contiguous bases of mRNA of a target gene associated with tumor or inflammation (hereinafter, sequence $X_1$), and a base sequence (hereinafter, complementary sequence $X_1'$) complementary to the sequence $X_1$, 1 to 90% of all sugars binding to the bases of the sequence $X_1$ and the complementary sequence $X_1'$ being ribose substituted by a modifying group at 2' position; and
a lipid bilayer membrane for coating the complex particle,
wherein constituent components of the lipid bilayer membrane are soluble in a polar organic solvent, and the constituent components of the lipid bilayer membrane, and the complex particle are dispersible in a liquid that contains the polar organic solvent in a specific concentration.

(32) The method for treating cancer or inflammatory disease according to the above (31), wherein the polar organic solvent is an alcohol.

(33) The method for treating cancer or inflammatory disease according to the above (31), wherein the polar organic solvent is ethanol.

(34) The method for treating cancer or inflammatory disease according to any one of the above (31) to (33), wherein the lead particle contains a cationic substance, and wherein the lipid bilayer membrane contains, as constituent components, a neutral lipid, and a lipid derivative, a fatty acid derivative, or an aliphatic hydrocarbon derivative of a water-soluble substance.

(35) A method for treating cancer or inflammatory disease, which comprises administering to a mammal a composition that includes:
a complex particle that contains, as constituent components, a cationic substance-containing lead particle, and an RNA that contains a sequence consisting of 15 to 30 contiguous bases of mRNA of a target gene associated with tumor or inflammation (hereinafter, sequence $X_1$), and a base sequence (hereinafter, complementary sequence $X_1'$) complementary to the sequence $X_1$, 1 to 90% of all sugars binding to the bases of the sequence $X_1$ and the complementary sequence $X_1'$ being ribose substituted by a modifying group at 2' position; and
a lipid bilayer membrane for coating the complex particle,
wherein the lipid bilayer membrane contains, as constituent components, a neutral lipid, and a lipid derivative, a fatty acid derivative, or an aliphatic hydrocarbon derivative of a water-soluble substance.

(36) The method for treating cancer or inflammatory disease according to the above (34) or (35), wherein the cationic substance is one or more compounds selected from N-[1-(2,3-dioleoylpropyl)]-N,N,N-trimethylammonium chloride, N-[1-(2,3-dioleoylpropyl)]-N,N-dimethylamine, N-[1-(2,3-dioleyloxypropyl)-N,N,N-trimethylammonium chloride, N-[1-(2,3-ditetradecyloxypropyl)]-N,N-dimethyl-N-hydroxyethylammonium bromide, and 3β-[N—(N'N'-dimethylaminoethyl)carbamoyl cholesterol.

(37) The method for treating cancer or inflammatory disease according to any one of the above (34) to (36), wherein the lipid derivative, the fatty acid derivative, or the aliphatic hydrocarbon derivative of a water-soluble substance is polyethylene glycol phosphatidyl ethanolamine.

(38) The method for treating cancer or inflammatory disease according to any one of the above (34) to (37), wherein the neutral lipid is egg yolk phosphatidylcholine.

(39) The method for treating cancer or inflammatory disease according to any one of the above (31) to (38), wherein the RNA is an RNA having an action of suppressing the expression of the target gene by utilizing RNA interference (RNAi).

(40) The method for treating cancer or inflammatory disease according to any one of the above (31) to (38), wherein the target gene associated with tumor or inflammation is a gene associated with angiogenesis.

(41) The method for treating cancer or inflammatory disease according to any one of the above (31) to (38), wherein the target gene associated with tumor or inflammation is a gene of any one of a vascular endothelial growth factor, a vascular endothelial growth factor receptor, a fibroblast growth factor, a fibroblast growth factor receptor, a platelet-derived growth factor, a platelet-derived growth factor receptor, a hepatocyte growth factor, a hepatocyte growth factor receptor, a Krüppel-like factor, an Ets transcription factor, a nuclear factor, and a hypoxia-inducible factor.

(42) The method for treating cancer or inflammatory disease according to any one of the above (31) to (41), wherein the mRNA is either human mRNA or mouse mRNA.

(43) A method for measuring a blood siRNA concentration, which comprises:
adding a reagent that forms a complex with nucleic acid to a siRNA-containing test solution, so as to form an electrically neutral complex with the siRNA;
separating the complex and dissolving the complex in a redissolving solution; and
analyzing the resulting solution by high-performance liquid chromatography so as to measure a concentration of the siRNA.

(44) The method for measuring a blood siRNA concentration according to the above (43), wherein the test solution includes a nucleic acid as IS that differs in number of bases from the siRNA being measured.

(45) The method for measuring a blood siRNA concentration according to the above (43) or (44), wherein a detecting device used for the high-performance liquid chromatography analysis is a mass spectroscope.

Effects of the Invention

By administering the composition of the present invention that comprises a lipid particle encapsulating an RNA that contains a sequence consisting of 15 to 30 contiguous bases of a target gene mRNA and a base sequence complementary to the sequence to a mammal or the like, the expression of the target gene can be suppressed.

MODE FOR CARRYING OUT THE INVENTION

Figure 1:
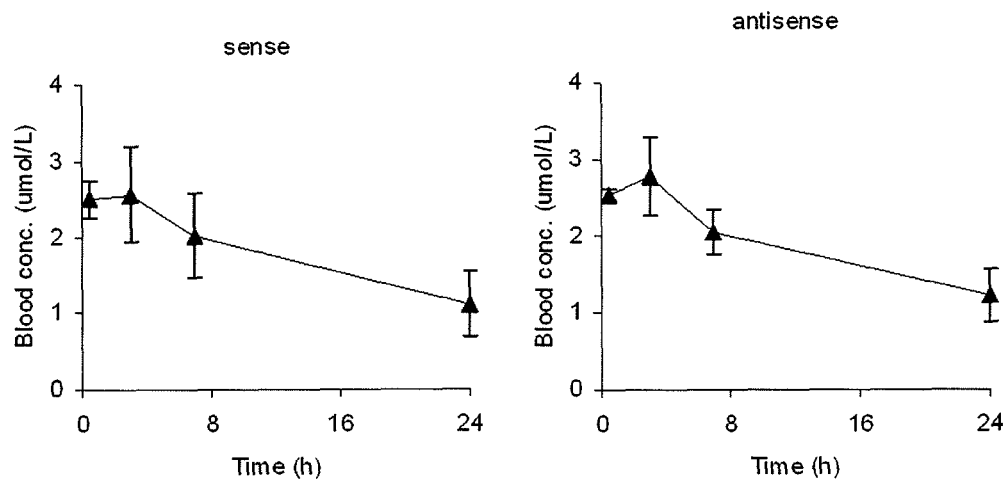
FIG. 1 shows blood RNA concentrations in response to administration of a preparation obtained in Example 1; the horizontal axis represents time (hours) after administration of the preparation; the vertical axis represents blood RNA concentration (μmol/L).

The target gene in the present invention is not particularly limited as long as it is a gene which produces and expresses mRNA in mammals. For example, the target gene is preferably a gene associated with tumor or inflammation, more preferably a gene associated with angiogenesis, and the like. Examples include genes that code for proteins such as a vascular endothelial growth factor (hereinafter, VEGF), a vascular endothelial growth factor receptor (hereinafter, VEGFR), a fibroblast growth factor, a fibroblast growth factor receptor, a platelet-derived growth factor, a platelet-derived growth factor receptor, a hepatocyte growth factor, a hepatocyte growth factor receptor, a Krüppel-like factor (hereinafter, KLF), an Ets transcription factor, a nuclear factor, and a hypoxia-inducible factor, and the like. Specific examples include VEGF gene, VEGFR gene, fibroblast growth factor gene, fibroblast growth factor receptor gene, platelet-derived growth factor gene, platelet-derived growth factor receptor gene, hepatocyte growth factor gene, hepatocyte growth factor receptor gene, KLF gene, Ets transcription factor gene, nuclear factor gene, hypoxia-inducible factor gene, and the like. The preferred target gene is, for example, VEGF gene, VEGFR gene, and KLF gene, more preferably KLF gene, further preferably KLF5 gene.

The KLF family is a family of transcriptional factors, which is characterized in that it has a zinc finger motif at the C-terminus thereof, and examples thereof that have been known include KLF1, KLF2, KLF3, KLF4, KLF5, KLF6, KLF7, KLF8, KLF9, KLF10, KLF11, KLF12, KLF13, KLF14, KLF15, KLF 16 and the like. It has been reported that, in mammals, the KLF family plays an important role in differentiation of various types of tissues or cells, such as erythrocytes, vascular endothelial cells, smooth muscle, skin, and lymphocytes, and also in formation of the pathologic conditions of various types of diseases such as cancer, cardiovascular diseases, cirrhosis, renal diseases, and immune-mediated diseases (The Journal of Biological Chemistry, Vol. 276, No. 37, pp. 34355-34358, 2001; Genome Biology, Vol. 4, No. 2, p. 206, 2003).

Among the KLF family members, KLF5 is also referred to as BTEB2 (basic transcriptional element binding protein 2) or IKLF (intestinal-enriched Krüppel-like factor). The expression of KLF5 in vascular smooth muscle is controlled at the development stage thereof. KLF5 is highly expressed in the vascular smooth muscle of a fetus, whereas its expression is not found in the vascular smooth muscle of a healthy adult. In addition, in the case of the smooth muscle of intima of a blood vessel regenerated after denudation by a balloon catheter, KLF5 is highly expressed. Also, in the smooth muscle in lesions due to arteriosclerosis or restenosis, KLF5 is expressed (Circulation, Vol. 102, No. 20, pp. 2528-2534, 2000).

VEGF, discovered by Ferrara and others in 1983, is a growth factor specific to vascular endothelial cells. In the same year, Senger and Dvorak, with several others, discovered a factor having vascular permeability activity, and they named this factor a VPF (vascular permeability factor). Amino acid sequence analysis of the proteins revealed that these were the same. VEGF facilitates growth by binding to receptors on the endothelial cells lining inside blood vessels. VEGF has activity not only in the formation of blood vessels during the fetal period, but in the formation of pathologic blood vessels. For example, when cancer grows to a certain size and becomes deficient in oxygen, VEGF and VFGF receptor production increases and induces angiogenesis. Further, the vascular permeability increasing effect is also considered to be a cause of cancerous ascites. VEGF also play a role in the formation of new blood vessels in the retina during the propagation of diabetes mellitus. Specifically, VEGF is a protein that forms new blood vessels. VEGF expression induced by a low-oxygen state thus has an important role in angiogenesis. Aside from its role in angiogenesis, involvement of VEGF factor is strongly indicated in explaining the mechanism of edema seen in tumor or inflammatory lesions and the like.

On the other hand, VEGFRs are present in vascular endothelial cells or cancer cells themselves. Upon binding to VEGF, the receptors themselves are phosphorylated (activated), signaling the cells to, for example, grow or migrate. It is known that inhibiting the receptor phosphorylation inhibits the signaling in the cells, and thus inhibits angiogenesis.

Examples of the target gene include B-CELL CLL/LYMPHOMA (hereinafter, bcl) genes, and the preferred target gene is, for example, bcl2 gene.

Bcl-2 is a mitochondria inner membrane protein that inhibits apoptotic cell death in some type of cell. Inhibition of apoptosis by high expression of Bcl-2 protein is considered to be a cause of diseases such as cancer and hematological malignant disease. In fact, large production of Bcl-2 protein is found in various solid cancers, including lymphatic sarcoma, prostate cancer, breast cancer, lung cancer, colon cancer, rectum cancer, and the like (T. J. McDonnell et al, *Cancer Research*, Dec. 15, 1992, Vol. 52, No. 24, p. 6940-6944). Involvement of Bcl-2 expression in apoptosis in the thymus gland is also indicated (Kanavaros et al., *Histol. Histopathol.* 16(4): 1005-12 (October 2001)).

Because of the apoptosis suppressing effect, cell death is not induced in cells that produce high levels of Bcl-2 protein, and as a result drug resistance to various anticancer agents occurs. On the other hand, suppressing Bcl-2 production in prostate cancer cells is known to suppress cell growth and helps induce apoptosis (Shi et al., *Cancer Biother. Radiopharm.*, 16(5): 421-9 (October 2001)). Thus, a method that suppresses Bcl-2 protein expression can be an effective therapeutic or preventive method in diseases that require the promotion of apoptosis for the cure, such as in solid cancers and hematological malignant diseases.

Examples of the RNA used in the present invention include an RNA that contains a sequence (hereinafter, sequence X) consisting of 15 to 30, preferably 17 to 25, and more preferably 19 to 23 contiguous bases of the above-mentioned target gene mRNA, and a base sequence (hereinafter, complementary sequence X') complementary to sequence X. For example, the RNA used in the present invention may be a double-stranded RNA that consists of a sequence X-containing sense strand, and a complementary sequence X'-containing antisense strand, or an RNA of a hairpin structure in which the sense strand and the antisense strand are linked to each other by a spacer oligonucleotide.

The sequence X-containing sense strand may be an RNA whose bases are solely sequence X (hereinafter, sequence X strand), or an RNA that contains a sequence X strand with 1 to 6, preferably 2 to 4 nucleotides which are the same or different and are added to the 3'-end and/or the 5'-end of the sequence X strand. The complementary sequence X'-containing antisense strand may be, for example, an RNA whose bases are solely complementary sequence X' (hereinafter, complementary sequence X' strand), or an RNA that includes the complementary sequence X' strand with 1 to 6, preferably 2 to 4 nucleotides which are the same or different and are added to the 3'-end and/or 5'-end of the complementary sequence X' strand.

The spacer oligonucleotide linking the sequence X-containing sense strand and the complementary sequence X'-containing antisense strand in the RNA of a hairpin structure preferably contains nucleotides of 6 to 12 bases, preferably with two uracils at the 5'-end of the sequence. An example of such a spacer oligonucleotide is an oligonucleotide with the base sequence UUCAAGAGA. Either of the two RNA portions that are linked to each other via the spacer oligonucleotide may be suitable as the RNA on the 5'-end side. Preferably, the sequence X-containing sense strand represents the 5'-end side.

The nucleotides and the spacer oligonucleotide added to the sequence X strand and the complementary sequence X' strand may contain one or more bases selected from guanine, adenine, cytosine, thymine, and uracil, and the sugar binding to each base may be any of ribose, deoxyribose, and ribose whose hydroxyl group at the 2' position is substituted by a modifying group. More preferably, the nucleotides added are one or two of urydylic acid (U) and deoxythymidylic acid (dT). The base sequence of the nucleotides added to the 3'-end of the sequence X strand may be the same as the base sequence of the nucleotides adjoining the sequence X in the mRNA of the target gene, and this structure is more preferable. Similarly, the base sequence of the nucleotides added to the 3'-end of the complementary sequence X' strand may be a base sequence complementary to the base sequence of the nucleotides adjoining the sequence X in the mRNA of the target gene, and this structure is more preferable.

More preferred examples of the RNA used in the present invention include (a) a double-stranded RNA that has a sense strand and an antisense strand containing sequence X and complementary sequence X', respectively, the sequence X being a sequence consisting of 19 to 21 contiguous bases of a target gene mRNA, the sense strand consisting of the sequence X strand and 2 to 4 nucleotides which are the same or different and are added to the 3'-end of the sequence X strand, the antisense strand consisting of the complementary sequence X' strand, and 2 to 4 nucleotides which are the same or different and are added to the 3'-end of the complementary sequence X' strand, (b) a double-stranded RNA that has a sense strand and an antisense strand containing sequence X and complementary sequence X', respectively, the sequence X being a sequence consisting of 23 to 25 contiguous bases of a target gene mRNA, the sense strand consisting of the sequence X strand, the antisense strand consisting of the complementary sequence X' strand, (c) a double-stranded RNA that has a sense strand and an antisense strand containing sequence X and complementary sequence X', respectively, the sequence X being a sequence consisting of 23 to 27 contiguous bases of a target gene mRNA, the sense strand consisting of the sequence X strand and 2 to 4 nucleotides which are the same or different and are added to the 3'-end of the sequence X strand, the antisense strand consisting of the complementary sequence X' strand and 2 to 4 nucleotides which are the same or different and are added to the 3'-end of the complementary sequence X' strand, the base sequence of the nucleotides added to the 3'-end of the complementary sequence X' strand being a base sequence complementary to the base sequence of the nucleotides adjoining the sequence X in the target gene mRNA, and the like.

Further, the RNA used in the present invention is preferably, for example, an RNA having an action of suppressing the expression of the target gene by utilizing RNA interference (RNAi).

Such an RNA suppressing the expression of the target gene by utilizing RNA interference (RNAi) is described below, by taking a Bcl2 gene expression-suppressing RNA as an example. RNAs that suppress expression of other genes also can be obtained using similar procedures.

The RNA suppressing the expression of bcl-2 gene can be designed based on the DNA base sequence (SEQ ID NO: 29) corresponding to the full-length mRNA of bcl-2 (Genbank Accession No. NM_000633). From the DNA base sequence, partial contiguous sequences of 15 to 30 bases, preferably 17 to 27 bases, more preferably 19 to 25 bases are removed. The GC content in the removed sequences is calculated, and sequences with the GC content of 20 to 80%, preferably 30% to 70%, more preferably 40 to 60% are selected. A base sequence with a T-to-U substitution is then obtained as sequence X. The bcl-2 gene expression-suppressing RNA is then obtained as a double-stranded RNA that has a sense strand containing the selected sequence X, and an antisense strand containing complementary sequence X' complementary to the sequence X, or as an RNA of a hairpin structure that contains the sense strand and the antisense strand linked to each other via a spacer oligonucleotide.

In the RNA used in the present invention, 1 to 90%, preferably 10 to 75%, more preferably 20 to 65%, most preferably 30 to 55% of all sugars binding to the bases of sequence X and complementary sequence X' are ribose substituted by a modifying group at 2' position.

As used herein, the substitution by a modifying group at the 2' position of the ribose means substitution of the hydroxyl group by a modifying group at 2' position. The modifying group may have the same or different configuration as the hydroxyl group at the 2' position of the ribose, and preferably has the same configuration as the hydroxyl group at the 2' position of the ribose.

The sugars binding to the bases of sequence X and complementary sequence X' are riboses or deoxyriboses, except for the ribose substituted by a modifying group at 2' position. Preferably, all sugars except for the ribose substituted by a modifying group at 2' position are ribose.

The RNA used in the present invention encompasses derivatives in which the oxygen atoms contained in the phosphate moiety, ester moiety, and the like in the ribonucleic acid structure is substituted with other atoms, for example, such as a sulfur atom.

The sugar binding to the base at the 5'-end of the RNA used in the present invention may be that in which the hydroxyl group at the 5' position is modified with a phosphate group, a modifying group, or a group that becomes a phosphate group or a modifying group by the action of a nucleolytic enzyme or the like in the body. Preferably, the hydroxyl group at the 5' position of the sugar binding to the base at the 5'-end of the sense strand is phosphorylated.

The sugar binding to the base at the 3'-end of the RNA used in the present invention may be that in which the hydroxyl group at the 3' position is modified with a phosphate group, a modifying group, or a group that becomes a phosphate group or a modifying group by the action of a nucleolytic enzyme or the like in the body.

Examples of the modifying group in the present invention include 2'-cyano, 2'-alkyl, 2'-substituted alkyl, 2'-alkenyl, 2'-substituted alkenyl, 2'-halogen, 2'-O-cyano, 2'-O-alkyl, 2'-O-substituted alkyl, 2'-O-alkenyl, 2'-O-substituted alkenyl, 2'-S-alkyl, 2'-S-substituted alkyl, 2'-S-alkenyl, 2'-S-substituted alkenyl, 2'-amino, 2'-NH-alkyl, 2'-NH-substituted alkyl, 2'-NH-alkenyl, 2'-NH-substituted alkenyl, 2'-SO-alkyl, 2'-SO-substituted alkyl, 2'-carboxy, 2'-CO-alkyl, —CO-substituted alkyl, —Se-alkyl, —Se-substituted alkyl, —SiH$_2$-alkyl, —SiH$_2$-substituted alkyl, 2'-ONO$_2$, 2'-NO$_2$, 2'-N$_3$, 2'-NH-alkyl, 2'-NH-substituted alkyl, 2'-amino acid residue (amino acid with the hydroxyl group removed from the carboxylic acid), and 2'-O-amino acid residue (having the same definition as above). The ribose with the substitution by a modifying group at 2' position in the present invention also encompasses bridged nucleic acids (BNAs) of a structure in which the modifying group at 2' position is bridged to the 4' carbon atom, specifically, locked nucleic acids (LNAs) in which the oxygen atom at 2' position is bridged to the 4' carbon atom via methylene, ethylene bridged nucleic acids (ENAs) [Nucleic Acid Research, 32, e175 (2004)], and the like.

The preferred modifying group in the present invention include 2'-cyano, 2'-halogen, 2'-O-cyano, 2'-alkyl, 2'-substituted alkyl, 2'-O-alkyl, 2'-O-substituted alkyl, 2'-O-alkenyl, 2'O-substituted alkenyl, —Se-alkyl, and —Se-substituted alkyl. More preferred examples include 2'-cyano, 2'-fluoro, 2'-chloro, 2'-bromo, 2'-trifluoromethyl, 2'-O-methyl, 2'-O-ethyl, 2'-O-isopropyl, 2'-O-trifluoromethyl, 2'-O-[2-(methoxy)ethyl], 2'-O-(3-aminopropyl), 2'-O-(2-[N,N-dimethyl]aminooxy)ethyl, 2'-O-[3-(N,N-dimethylamino)propyl], 2'-O-[2-[2-(N,N-Dimethylamino) ethoxy]ethyl], 2'-O-[2-(methylamino)-2-oxoethyl], 2'-Se-methyl, and the like. Even more preferred are 2'-O-methyl, 2'-O-ethyl, 2'-fluoro, and the like. 2'-O-methyl and 2'-O-ethyl are most preferable.

The preferred range of the modifying group in the present invention may be defined based on its size. Modifying groups of a size corresponding to the size of fluoro to the size of —O-butyl are preferable, and modifying groups of a size corresponding to the size of —O-methyl to the size of —O-ethyl are more preferable.

Examples of the alkyl in the modifying group include linear or branched alkyl having 1 to 6 carbon atoms, for example, such as methyl, ethyl, propyl, isopropyl, butyl, isobutyl, sec-butyl, tert-butyl, pentyl, isopentyl, neopentyl, tert-pentyl, and hexyl. Preferred examples include methyl, ethyl, propyl, isopropyl, isobutyl, sec-butyl, tert-butyl, pentyl, neopentyl, tert-pentyl, and the like. Examples of the alkenyl in the modifying group include linear or branched alkenyl having 1 to 6 carbon atoms, for example, such as vinyl, allyl, and isopropenyl.

Examples of the halogen include a fluorine atom, a chlorine atom, a bromine atom, and an iodine atom.

Examples of the amino acid include aliphatic amino acids (specifically, glycine, alanine, valine, leucine, isoleucine, and the like), hydroxy amino acids (specifically, serine, threonine, and the like), acidic amino acids (specifically, aspartic acid, glutamic acid, and the like), acidic amino acid amides (specifically, asparagine, glutamine, and the like), basic amino acids (specifically, lysine, hydroxylysine, arginine, ornithine, and the like), sulfur-containing amino acids (specifically, cysteine, cystine, methionine, and the like), imino acids (specifically, proline, 4-hydroxy proline, and the like), and the like.

Examples of the substituents of the substituted alkyl and the substituted alkenyl include halogen (having the same definition as above), hydroxy, sulfanyl, amino, oxo, —O-alkyl (having the same definition as above), —S-alkyl (having the same definition as above), —NH-alkyl (having the same definition as above), dialkylaminooxy (the two alkyls may be the same or different, and have the same definition as above), dialkylamino (the two alkyls may be the same or different, and have the same definition as above), dialkylaminoalkyleneoxy (the two alkyls may be the same or different, and have the same definition as above; the alkylene means a group wherein the hydrogen removed from above-defined alkyl), and the like, and in number of preferably 1 to 3.

The RNA used in the present invention does not depend a method of production, raw material, and intermediate, and also encompasses, for example, RNAs using DNA or deoxyribose as the raw material or intermediate, as long as the end products have the same structural formula. Specifically, the ribose removed the oxygen atom at the 2' position in the present invention encompasses deoxyribose, and the ribose substituted by a modifying group at 2' position encompasses a deoxyribose in which the hydrogen at the 2' position is replaced with a modifying group.

In the RNA used in the present invention, it is preferable that the riboses substituted by a modifying group at 2' position be distributed so that the fewest possible number of these riboses occur adjacently. More preferably, the riboses substituted by a modifying group at 2' position are combined and distributed in such a manner that they occur in every other position or every two or three positions, and do not occur adjacently. Particularly, for the riboses binding to the bases of sequence X, it is more preferable that 30 to 55% of the riboses have a substitution by a modifying group at 2' position, and occur in every two riboses, and do not occur adjacently.

Further, in the complementary base pairs of sequence X and complementary sequence X', it is preferable that the riboses substituted by a modifying group at 2' position occur only on one ribose of these sequences instead of both. Further, in this preferred structure, the riboses substituted by a modifying group at 2' position are most preferably combined and distributed in such a manner that they occur in every two or three or four riboses, and do not occur adjacently.

The RNA used in the present invention may be produced using known RNA or DNA synthesis methods or known RNA or DNA modification methods. For example, the RNA can be obtained by using chemical synthesis services provided by, for example, Hokkaido System Science Co., Ltd.

The lipid particle in the composition of the present invention (hereinafter, "lipid particle A) is preferably a lipid particle that encapsulates an RNA that contains a sequence consisting of 15 to 30 contiguous bases of a target gene mRNA and a base sequence complementary to the sequence. The lipid particle A is not particularly limited, as long as it is capable of reaching a tissue or an organ containing an expression site of the target gene. However, the lipid particle A should be appropriately selected, because some lipid particles reach tissues or organs more easily than others.

Examples of lipid particle A used in the present invention include liposome and lipid micelle.

Examples of lipid particle A used in the present invention include a lipid particle produced by reverse-phase evaporation treatment of a water-in-oil type (W/O) emulsion formed by adding a polyethylene glycolated lipid, a neutral lipid, and water to a dispersion of a cationic lipid/RNA complex in a hydrophobic organic solvent layer (see Japanese translation of PCT international application, No. 2002-501511), a lipid particle produced from an RNA-encapsulating lipid particle prepared by lowering ethanol concentration after adding lipid (in ethanol) to a solution of RNA dissolved in an acidic electrolyte aqueous solution, which RNA-encapsulating lipid particle is then subjected to dialysis at an increased sample pH to remove the RNA adhering to the lipid particle surface (see Japanese translation of PCT international application, No. 2002-501511, and Biochimica et Biophysica Acta, 2001, Vol. 1510, p. 152-166), a lipid particle including complex particles that contain a lead particle and the RNA, and a lipid bilayer membrane for encapsulating the complex particles (see WO02/28367, and WO2006/080118), and the like. The lipid particle A is preferably a lipid particle including complex particles that include a lead particle and the RNA, and a lipid bilayer membrane for encapsulating the complex particles. It is more preferable that the constituent components of the lipid bilayer membrane be soluble in a polar organic solvent, and that the constituent components of the lipid bilayer membrane and the complex particles be dispersible in a liquid that contains the polar organic solvent in a specific concentration. It is also preferable that the lipid particle A be a lipid particle that includes complex particles containing a cationic substance-containing lead particle and the RNA as constituent components, and a lipid bilayer membrane for coating the complex particles, and in which the lipid bilayer membrane contains, as constituent components, a neutral lipid, and a lipid derivative, a fatty acid derivative, or an aliphatic hydrocarbon derivative of a water-soluble substance. More preferably, the constituent components of the lipid bilayer membrane are soluble in a polar organic solvent, and the constituent components of the lipid bilayer membrane and the complex particles are dispersible in a liquid that contains the polar organic solvent in a specific concentration. As used herein, the terms "disperse" means dispersing insolubly.

It has been reported that the lipid particles exemplified above can be delivered to tumor- or inflammation-bearing tissues or organs, specifically, to solid tumors, solid cancers, or inflammation sites in blood vessels or in the vicinity of blood vessels, and the like. The foregoing lipid particles can therefore be preferably used when the target gene is a gene associated with tumor or inflammation.

Further, the lipid particles exemplified above are reported to have high retention in the blood. Thus, these lipid particles have a high possibility of being delivered to any tissue or organ through systemic circulation, and thus a gene that can be targeted is not limited.

The lead particle in the present invention is a fine particle of, for example, lipid assembly, liposome, polymeric micelle, and the like, preferably a fine particle of liposome. The lead particle in the present invention may be a complex as a combination of two or more of a lipid assembly, a liposome, a polymeric micelle, and the like. For example, the lead particle may be a polymeric micelle as a complex that contains the constituent component lipids of a lipid assembly, a liposome, and the like, or a lipid assembly, liposome, and the like as a complex that contains the constituent component polymer of a polymeric micelle.

The lipid assembly or the liposome (hereinafter, liposome B) as the lead particle may contain components, for example, such as a lipid and/or a surfactant, preferably a lipid, or a combination of lipid and surfactant. The lipid is not particularly limited, and may be any of a simple lipid, a complex lipid and a derived lipid, and examples thereof include a phospholipid, a glyceroglycolipid, a sphingoglycolipid, a sphingoid, a sterol, a cationic lipid, and the like. Preferred examples include a phospholipid and a cationic lipid. Further, examples of the lipid also include surfactants (the same definition as the surfactant described below) or lipid derivatives of polymer (the same definition as the polymer described below, specifically, dextran, etc.), a polyoxyethylene derivative (specifically, polyethylene glycol, etc.) or the like. Examples of the surfactant include a nonionic surfactant, an anionic surfactant, a cationic surfactant, a zwitterionic surfactant, and the like.

Examples of the phospholipid as the constituting lipid of the lead particle include natural and synthetic phospholipids such as phosphatidylcholine (specifically, soybean phosphatidylcholine, egg yolk phosphatidylcholine (EPC), distearoyl phosphatidylcholine, dipalmitoyl phosphatidylcholine, dimyristoyl phosphatidylcholine, dioleoyl phosphatidylcholine, etc.), phosphatidylethanolamine (specifically, distearoyl phosphatidylethanolamine (DSPE), dipalmitoyl phosphatidylethanolamine, dioleoyl phosphatidylethanolamine, etc.), glycerophospholipid (specifically, phosphatidylserine, phosphatidic acid, phosphatidylglycerol, phosphatidylinositol, lysophosphatidylcholine, etc.) sphingophospholipid (specifically sphingomyelin, ceramide phosphoethanolamine, ceramide phosphoglycerol, ceramide phosphoglycerophosphate, etc.), glycerophosphono lipid, sphingophosphonolipid, natural lecithin (specifically, egg yolk lecithin, soybean lecithin, etc.), and hydrogenated phospholipid (specifically hydrogenated soybean phosphatidylcholine, etc.).

Examples of the glyceroglycolipid as the constituting lipid of the lead particle include sulfoxyribosyl glyceride, diglycosyl diglyceride, digalactosyl diglyceride, galactosyl diglyceride, glycosyl diglyceride and the like.

Examples of the sphingoglycolipid as the constituting lipid of the lead particle include galactosyl cerebroside, lactosyl cerebroside, ganglioside, and the like.

Examples of the sphingoid as the constituting lipid of the lead particle include sphingan, icosasphingan, sphingosine, a derivative thereof, and the like. Examples of the derivative thereof include those in which —$NH_2$ of sphingan, icosasphingan, sphingosine or the like is replaced with —NHCO$(CH_2)_xCH_3$ (in the formula, x represents an integer of 0 to 18, in particular, 6, 12 or 18 is preferred), and the like.

Examples of the sterol as the constituting lipid of the lead particle include cholesterol, dihydrocholesterol, lanosterol, β-sitosterol, campesterol, stigmasterol, brassicasterol, ergocasterol, fucosterol, 3β-[N—(N',N'-dimethylaminoethyl)carbamoyl]cholesterol (DC-Chol), and the like.

Examples of the cationic lipid as constituting lipid of the lead particle include N-[1-(2,3-dioleoylpropyl)]-N,N,N-trimethylammonium chloride (DOTAP), N-[1-(2,3-dioleoylpropyl)]-N,N-dimethylamine (DODAP), N-[1-(2,3-dioleyloxypropyl)-N,N,N-trimethylammonium chloride (DOTMA), 2,3-dioleyloxy-N-[2-(sperminecarboxyamido) ethyl]-N,N-dimethyl-1-propanaminium trifluoroacetate (DOSPA), N-[1-(2,3-ditetradecyloxypropyl)]-N,N-dimethyl-N-hydroxyethylammonium bromide (DMRIE), N-[1-(2,3-dioleyloxypropyl)]-N,N-dimethyl-N-hydroxyethylammonium bromide (DORIE), and the like.

Examples of the nonionic surfactant forming the lead particle include polyoxyethylene sorbitan monooleate (specifically, Polysorbate 80, etc.), polyoxyethylene polyoxypropylene glycol (specifically, Pluronic F68, etc.), a sorbitan fatty acid ester (specifically, sorbitan monolaurate, sorbitan monooleate, etc.), a polyoxyethylene derivative (specifically, polyoxyethylene hydrogenated castor oil 60, polyoxyethylene lauryl alcohol, etc.), a glycerol fatty acid ester, and the like.

Examples of the anionic surfactant forming the lead particle include acylsarcosine, sodium alkylsulfate, alkylbenzene sulfonate, a sodium fatty acid having 7 to 22 carbon atoms and the like. Specific examples include sodium dodecyl sulfate, sodium lauryl sulfate, sodium cholate, sodium deoxycholate, sodium taurodeoxycholate, and the like.

Examples of the cationic surfactant forming the lead particle include an alkylamine salt, an acylamine salt, a quaternary ammonium salt, an amine derivative, and the like. Specific examples include benzalkonium chloride, an acylaminoethyldiethylamine salt, an N-alkylpolyalkylpolyamine salt, a polyethylene polyamide of fatty acid, cetyltrimethylammonium bromide, dodecyltrimethylammonium bromide, alkylpolyoxyethyleneamine, N-alkylaminopropylamine, a triethanolamine fatty acid ester, and the like.

Examples of the zwitterionic surfactant forming the lead particle include 3-[(3-cholamidopropyl)dimethylammonio]-1-propane sulfonate, N-tetradecyl-N,N-dimethyl-3-ammonio-1-propane sulfonate, and the like.

In the liposome B, these lipids and surfactants are used alone or in combinations of two or more, and preferably they are used in combinations of two or more. As the combination in the case where they are used in combinations of two or more, for example, a combination of two or more components selected from a hydrogenated soybean phosphatidylcholine, a polyethylene glycolated phospholipid, and cholesterol, a combination of two or more components selected from distearoyl phosphatidylcholine, a polyethylene glycolated phospholipid, and cholesterol, a combination of EPC and DOTAP, a combination of EPC, DOTAP, and a polyethylene glycolated phospholipid, a combination of EPC, DOTAP, cholesterol, and a polyethylene glycolated phospholipid, and the like can be exemplified.

Further, the liposome B may contain a membrane stabilizer such as a sterol including cholesterol, an antioxidant such as tocopherol or the like, as needed. The stabilizers may be used either alone or in combinations of two or more.

Examples of the lipid assembly include a spherical micelle, a spherical reversed micelle, a sausage-shaped micelle, a sausage-shaped reversed micelle, a plate-shaped micelle, a plate-shaped reversed micelle, hexagonal I, hexagonal II and an associated product of two or more lipid molecules, and emulsion particles (for example, oil-in-water (o/w) emulsion particles such as a fat emulsion, an emulsion of a nonionic surfactant and soybean oil, a lipid emulsion, and a lipid nanosphere, water-in-oil-in-water (w/o/w) emulsion particles, and the like).

The polymer micelle may be one or more micelles selected from, for example, protein, albumin, dextran, polyfect, chitosan, dextran sulfate; and polymers, for example, such as poly-L-lysine, polyethyleneimine, polyaspartic acid, a copolymer of styrene and maleic acid, a copolymer of isopropylacrylamide and acrylpyrrolidone, polyethylene glycol (PEG)-modified dendrimer, polylactic acid, polylactic acid polyglycolic acid, and polyethylene glycolated polylactic acid, and a salt thereof.

Here, the salt of the polymer includes, for example, a metal salt, an ammonium salt, an acid addition salt, an organic amine addition salt, an amino acid addition salt, and the like. Examples of the metal salt include alkali metal salts such as a lithium salt, a sodium salt and a potassium salt; alkaline earth metal salts such as a magnesium salt and a calcium salt; an aluminum salt; a zinc salt, and the like. Examples of the ammonium salt include salts of ammonium, tetramethylammonium, and the like. Examples of the acid addition salt include inorganates such as a hydrochloride, a sulfate, a nitrate, and a phosphate, and organates such as an acetate, a maleate, a fumarate, and a citrate. Examples of the organic amine addition salt include addition salts of morpholine, piperidine, and the like, and examples of the amino acid addition salt include addition salts of glycine, phenylalanine, aspartic acid, glutamic acid, lysine, and the like.

Further, the lead particle in the present invention preferably contains a lipid derivative or a fatty acid derivative of one or more substance(s) selected from, for example, sugars, peptides, nucleic acids and water-soluble polymers or a surfactant or the like. The lipid derivative or the fatty acid derivative of one or more substance(s) selected from sugars, peptides, nucleic acids and water-soluble polymers or the surfactant may be used as a constituent component of the lead particle or may be used by adding it to the lead particle.

Preferred examples of the lipid derivative or the fatty acid derivative of one or more substance(s) selected from sugars, peptides, nucleic acids and water-soluble polymers or the surfactant include a glycolipid or a lipid derivative or a fatty acid derivative of a water-soluble polymer, and more preferred examples thereof include a lipid derivative or a fatty acid derivative of a water-soluble polymer. The lipid derivative or the fatty acid derivative of one or more substance(s) selected from sugars, peptides, nucleic acids and water-soluble polymers or the surfactant is preferably a substance having a dual character that a part of the molecule has a property of binding to another constituent component(s) of the lead particle due to, for example, hydrophobic affinity, electrostatic interaction or the like, and other part has a property of binding to a solvent used in the production of the lead particle due to, for example, hydrophilic affinity, electrostatic interaction or the like.

Examples of the lipid derivative or the fatty acid derivative of a sugar, a peptide or a nucleic acid include those comprising a sugar such as sucrose, sorbitol or lactose, a peptide such as a casein-derived peptide, an egg white-derived peptide, a soybean-derived peptide or glutathione, a nucleic acid such as DNA, RNA, plasmid, siRNA or ODN, and any of the lipid illustrated in the above-mentioned definition of the lead particle or a fatty acid such as stearic acid, palmitic acid, myristic acid or lauric acid bonded to each other and the like.

Examples of the lipid derivative or the fatty acid derivative of a sugar include the glyceroglycolipids and the sphingoglycolipids illustrated in the above-mentioned definition of the lead particle and the like.

Examples of the lipid derivative or the fatty acid derivative of a water-soluble polymer include those comprising polyethylene glycol, polyglycerol, polyethyleneimine, polyvinyl alcohol, polyacrylic acid, polyacrylamide, oligosaccharide, dextrin, a water-soluble cellulose, dextran, chondroitin sulfate, polyglycerol, chitosan, polyvinylpyrrolidone, polyaspartate amide, poly-L-lysine, mannan, pullulan, oligoglycerol or the like or a derivative thereof and any of the lipid illustrated in the above-mentioned definition of the lead particle or a fatty acid such as stearic acid, palmitic acid, myristic acid or lauric acid bonded to each other and the like. More preferably, a lipid derivative or a fatty acid derivative of a polyethylene glycol derivative or a polyglycerol derivative can be exemplified, and further more preferably, a lipid derivative or a fatty acid derivative of a polyethylene glycol derivative can be exemplified.

Examples of the lipid derivative or the fatty acid derivative of a polyethylene glycol derivative include a polyethylene glycolated lipid [specifically, polyethylene glycol phosphatidyl ethanolamine (more specifically, 1,2-distearoyl-sn-glycero-3-phosphoethanolamine-N-[methoxy(polyethylene glycol)-2000] (PEG-DSPE) and the like), polyoxyethylene hydrogenated castor oil 60, Cremophor EL and the like), a polyethylene glycol sorbitan fatty acid ester (specifically, polyoxyethylene sorbitan monooleate and the like), a polyethylene glycol fatty acid ester and the like, and more preferred examples include a polyethylene glycolated lipid.

Examples of the lipid derivative or the fatty acid derivative of a polyglycerol derivative include a polyglycerolated lipid (specifically, polyglycerol phosphatidyl ethanolamine and the like), a polyglycerol fatty acid ester and the like, and more preferred examples include a polyglycerolated lipid.

Examples of the surfactant include the surfactants illustrated in the above-mentioned definition of the lead particle, a polyethylene glycol alkyl ether and the like, and preferred examples thereof include polyoxyethylene polyoxypropylene glycol, a glycerol fatty acid ester, a polyethylene glycol alkyl ether and the like.

The lead particle preferably has a positive electric charge. The "positive electric charge" as used herein includes an electric charge, surface polarization and the like which generate electrostatic attraction to an electric charge in the above-mentioned RNA, intramolecular polarization and the like. In order for the lead particle to have a positive electric charge, the lead particle preferably contains a cationic substance, more preferably contains a cationic lipid.

The cationic substance to be contained in the lead particle is a substance exhibiting a cationic nature, however, even if it is an amphoteric substance having both cationic group and anionic group, the relative electronegativity varies depending on the pH, bonding to another substance or the like, therefore, the amphoteric substance can be classified into a cationic substance as the case may be. These cationic substances may be used as a constituent component of the lead particle or may be used by adding it to the lead particle.

Examples of the cationic substance include the cationic substances among those illustrated in the above-mentioned definition of the lead particles (specifically, a cationic lipid, a cationic surfactants (the same definition as above), a cationic polymer and the like), a protein or a peptide which shows cationic nature at a pH equal to or less than an isoelectric point, and the like. More preferably, one or more substances selected from N-[1-(2,3-dioleoylpropyl)]-N,N,N-trimethylammonium chloride, N-[1-(2,3-dioleoylpropyl)]-N,N-dimethylamine, N-[1-(2,3-dioleyloxypropyl)-N,N,N-trimethylammonium chloride, N-[1-(2,3-ditetradecyloxypropyl)]-N,N-dimethyl-N-hydroxyethylammonium bromide and 3β-[N—(N',N'-dimethylaminoethyl)carbamoyl]cholesterol can be exemplified.

Examples of the cationic substance in lipid include DOTAP, DODAP, DOTMA, DOSPA, DMRIE, DORIE, DC-Chol and the like.

Examples of the cationic polymer include poly-L-lysine, polyethyleneimine, polyfect, chitosan and the like.

The protein or the peptide which shows cationic nature at a pH equal to or less than an isoelectric point is not particularly limited as long as it is a protein or a peptide which shows cationic nature at a pH equal to or less than the isoelectric point of the substance. Examples thereof include albumin, orosomucoid, globulin, fibrinogen, pepsin, ribonuclease T1 and the like.

The lead particle in the present invention can be produced by or in accordance with a known production method or a method similar to that, and a lead particle produced by any production method can be used. For example, liposome B, which is one type of the lead particle, a known liposome preparation method can be applied. As the known liposome preparation method, for example, liposome preparation method by Bangham, et al. [see "Journal of Molecular Biology" (J. Mol. Biol.), Vol. 13, pp. 238-252 (1965)], an ethanol injection method [see "Journal of Cell Biology" (J. Cell Biol.), Vol. 66, pp. 621-634 (1975)], a French press method [see "FEBS Letters" (FEBS Lett.), Vol. 99, pp. 210-214 (1979)], a freeze-thaw method [see "Archives of Biochemistry and Biophysics" (Arch. Biochem. Biophys.), Vol. 212, pp. 186-194 (1981)], a reverse phase evaporation method [see "Proceedings of the National Academy of Science United States of America" (Proc. Natl. Acad. Sci. USA), Vol. 75, pp. 4194-4198 (1978)], a pH gradient method (see, for example, Japanese Patent No. 2,572,554, Japanese Patent No. 2,659,136, etc.) and the like. As a solution for dispersing liposome B in the production of the liposome B, for example, water, an acid, an alkali, any of various buffers, a physiological saline solution, an amino acid infusion or the like can be used. Further, in the production of the liposome B, it is also possible to add an antioxidant such as citric acid, ascorbic acid, cysteine or ethylenediamine tetraacetic acid (EDTA), an isotonic agent such as glycerol, glucose, sodium chloride or the like. Further, the liposome can also be produced by dissolving a lipid or the like in, for example, an organic solvent such as ethanol, distilling off the solvent, adding a physiological saline solution or the like and stirring the mixture by shaking, thereby forming the liposome B.

Further, surface improvement of the liposome can be optionally carried out using, for example, a nonionic surfactants (the same definition as above), a cationic surfactants (the same definition as above), an anionic surfactants (the same definition as above), a polymer, a polyoxyethylene derivative or the like, and such a surface-improving liposome is also used as a constituent component of the lead particles such as liposome B in the present invention [see "Stealth Liposomes", edited by D. D. Lasic and F. Martin, CRC Press Inc., USA, pp. 93-102 (1995)]. Examples of the polymer to be used for surface improvement include dextran, pullulan, mannan, amylopectin, hydroxyethylstarch and the like. Examples of the polyoxyethylene derivative include Polysorbate 80, Pluronic F68, polyoxyethylene hydrogenated castor oil 60, polyoxyethylene lauryl alcohol, PEG-DSPE and the like. The surface improvement of the lead particles such as liposome B can be carried out by the methods of incorporating lipid derivative or a fatty acid derivative of one or more substance(s) selected from sugars, peptides, nucleic acids and water-soluble polymers or a surfactant in the lead particles.

An average particle diameter of the liposome B can be freely selected upon demand. It is preferable to adjust the average particle diameter to a diameter of the lead particle shown below. Examples of a method of adjusting the average particle diameter include an extrusion method and a method in which a large multilamellar liposome vesicle (MLV) is mechanically pulverized (specifically using Manton-gaulin, a microfluidizer or the like) (see "Emulsion and Nanosuspensions for the Formulation of Poorly Soluble Drugs", edited by R. H. Muller, S. Benita and B. Bohm, Scientific Publishers, Stuttgart, Germany, pp. 267-294, 1998) and the like.

In addition, the method of producing a complex obtained by combining two or more substances selected from, for example, a lipid assembly, liposome B, a polymer micelle, and the like, which constitute the lead particle, may be, for example, a production method in which, for example, a lipid, a polymer or the like are only mixed in water. At this time, a granulation step, a sterilization step or the like can be further added as needed. Further, it is also possible to perform the formation of the complex in any of various solvents such as acetone or ether.

As for the size of the lead particle in the present invention, an average particle diameter is preferably several nanometers to several tens micrometers, more preferably about 10 nm to 1000 nm, further more preferably about 50 nm to 300 nm.

Examples of the constituent components of the lipid bilayer membrane for coating the complex particles that contain the lead particle and the RNA in the present invention include the lipids, the surfactants, and the like illustrated in the above-mentioned definition of the lead particle, and preferred examples thereof include a neutral lipid among the lipids and the surfactants. The neutral lipid as used herein means a lipid excluding the cationic substance and cationic surfactant in the lipids illustrated in the cationic substance in the case where the lead particle has a positive electric charge described above, and the anionic lipid and the anionic surfactant illustrated in the adhesion-competitive agent described below among the lipids and surfactants, and preferred examples of the neutral lipid include a phospholipid, a glyceroglycolipid, a sphingoglycolipid, and the like. More preferred examples thereof include a phospholipid, and further more preferred examples thereof include EPC. These lipids or surfactants may be used either alone or in combinations of two or more.

Further, the constituent components of the lipid bilayer membrane for coating the complex particles are preferably soluble in a polar organic solvent, and are preferably dispersible in a liquid that contains the polar organic solvent in a specific concentration. The concentration of the polar solvent in a liquid that contains the polar solvent in a specific concentration is preferably such that the constituent components of the lipid bilayer membrane are dispersible, and that the complex particles are also dispersible. Examples of the polar organic solvent include alcohols such as methanol, ethanol, n-propanol, 2-propanol, n-butanol, 2-butanol, and tert-butanol, glycols such as glycerol, ethylene glycol, and propylene glycol, polyalkylene glycols such as polyethylene glycol, and the like. Alcohol is preferable, and ethanol is more preferable.

Examples of solvents other than the polar organic solvent contained in the polar organic solvent-containing liquid in the present invention include water, liquid carbon dioxide, liquid hydrocarbon, halogenated carbon, halogenated hydrocarbon, and the like, of which water is preferable. Further, the solvent may include other components, including ions and buffers. One or two or more solvents may be used. When two or more solvents are used, the solvents combined are preferably compatible to each other.

Further, preferred examples of the lipid to be used in the lipid bilayer membrane for coating the complex particles include a synthetic lipid and the like. Examples of the synthetic lipid include fluorinated phosphatidylcholine, fluorinated surfactants, dialkylammonium bromide, and the like. These may be used alone or in combination with another lipid or the like.

Further, the lipid bilayer membrane for coating the complex particles preferably contains a lipid derivative, a fatty acid derivative, or an aliphatic hydrocarbon derivative of a water-soluble substance, or the surfactant. Examples of the lipid derivative, the fatty acid derivative, or the aliphatic hydrocarbon derivative of a water-soluble substance include the above-mentioned lipid derivative or fatty acid derivative of one or more substances selected from sugars, peptides, nucleic acids, and water-soluble polymers, or the aliphatic hydrocarbon derivative of one or more substances selected from sugars, peptides, nucleic acids, and water-soluble polymers. The lipid derivative, the fatty acid derivative, or the aliphatic hydrocarbon derivative of a water-soluble substance is more preferably a lipid derivative or a fatty acid derivative of the water-soluble polymers, further preferably polyethylene glycolated phospholipid, most preferably polyethylene glycolated phosphatidyl ethanolamine. Examples of the aliphatic hydrocarbon derivative of a water-soluble substance in the present invention include those including a water-soluble substance bonded to, for example, an alcoholic residue of a long-chain aliphatic alcohol, polyoxypropylene alkyl, a glycerin fatty acid ester, and the like.

Examples of the aliphatic hydrocarbon derivative of a sugar, a peptide or a nucleic acid include an aliphatic hydrocarbon derivative of a sugar such as sucrose, sorbitol or lactose, a peptide such as a casein-derived peptide, an egg white-derived peptide, a soybean-derived peptide or glutathione, a nucleic acid such as DNA, RNA, plasmid, siRNA or ODN.

Examples of the aliphatic hydrocarbon derivative of a water-soluble polymer include an aliphatic hydrocarbon derivative of polyethylene glycol, polyglycerol, polyethyleneimine, polyvinyl alcohol, polyacrylic acid, polyacrylamide, oligosaccharide, dextrin, a water-soluble cellulose, dextran, chondroitin sulfate, polyglycerol, chitosan, polyvinylpyrrolidone, polyaspartate amide, poly-L-lysine, mannan, pullulan, oligoglycerol or the like or a derivative thereof, and more preferred examples thereof include an aliphatic hydrocarbon derivative of a polyethylene glycol derivative or a polyglycerol derivative, and more preferred examples thereof include an aliphatic hydrocarbon derivative of a polyethylene glycol derivative.

In the case where the lead particle is a fine particle containing liposome B as a constituent component, a substance which contains complex particles containing the liposome B and the above-mentioned RNA as constituent components and a lipid bilayer membrane for coating the complex particles becomes lipid particle A, which is classified into liposome in a narrow sense based on its structure. Even if the lead particle is different from a fine particle containing the liposome B as a constituent component, the lead particle is coated with a lipid bilayer membrane, therefore, the resulting substance is classified into liposome in a wide sense. In the present invention, it is more preferred that the lead particle is also a fine particle containing the liposome B.

The complex particles containing the lead particle and the RNA as constituent components in the present invention can be produced by adhering or encapsulating the RNA to or into the lead particle after or concurrently with the production of the lead particle. Further, lipid particle A can be produced by coating the complex particles with the lipid bilayer membrane after or concurrently with the production of the complex particles. The lipid particle A can be produced by or in accordance with a known production method described in, for example, Published Japanese translation of a PCT international application No. 2002-508765, Published Japanese translation of a PCT international application No. 2002-501511, "Biochimica et Biophysica Acta", Vol. 1510, pp. 152-166 (2001), and International Publication No. WO 02/28367, or can be produced by a production method including a step of dispersing the complex particles and coating layer components in a liquid which contains a polar organic solvent in which the coating layer components are soluble at a concentration at which the complex particles are not dissolved and the coating layer components are present in a dispersed state after the complex particles are produced by adhering or encapsulating the RNA to or into the lead particle, and a step of coating the complex particles with the coating layer components. It is preferred that the complex particles containing the lead particle and the RNA as constituent components in the present invention is produced after or concurrently with the production of the lead particle in water, by mixing RNA which is dispersed or dissolved in the optional liquid to the lead particle, then by adhering or encapsulating the RNA to or into the lead particle, or produced after the production of the lead particle in water, by mixing RNA which is dispersed or dissolved in the water to the lead particle, then by adhering the RNA to the lead particle, and it is more preferred that the complex particles is produced after the production of the lead particle in water, by mixing RNA which is dispersed or dissolved in the water to the lead particle, then by adhering the RNA to the lead particle.

As a preferred production method of the lipid particle A in the composition of the present invention, the following production method including a step of producing complex particles containing as constituent components a lead particle and the RNA (step 1) and a step of coating the complex particles with a lipid bilayer membrane (step 2 or step 3) can be exemplified.

Step 1) Step of Producing Complex Particles Containing as Constituent Components a Lead Particle and the RNA Lead particles are dispersed in a solvent such as water, the RNA dispersed or dissolved by mixing so as to be contained in the liquid in which the lead particles are dispersed, and the RNA is adhered to the lead particles. In the step 1, in order to suppress the aggregation of the lead particles, the lead particles are preferably lead particles containing an aggregation-suppressing substance, and more preferably the lead particles contain as the aggregation-suppressing substance, the above-mentioned lipid derivative or fatty acid derivative of one or more substance(s) selected from sugars, peptides, nucleic acids and water-soluble polymers or the surfactant. Further, in the case where the lead particles have a positive electric charge, the RNA and an adhesion-competitive agent are allowed to coexist in the liquid in which the lead particles are dispersed, and the adhesion-competitive agent may be adhered to the lead particles as well as the RNA. Further, also in the case where the lead particles are lead particles containing the aggregation-suppressing substance, in order to further suppress the aggregation of the lead particles, the adhesion-competitive agent may be used. In the combination of the lead particles and the RNA, it is preferred that a combination in which the complex particles are dispersible in the liquid containing a polar organic solvent is selected, and it is more preferred that the solubility of the complex particles in the polar organic solvent is lower than that of the constituent components of the lipid bilayer membrane to be used in the step 2 or 3. It is further more preferred that a combination in which the polar organic solvent can be contained in a liquid at such a concentration that the constituent components of the lipid bilayer membrane are dispersible and the complex particles are dispersible is selected.

Examples of the adhesion-competitive agent include an anionic substance and the like, and the anionic substance includes a substance electrostatically adhered to the lead particles due to the electrostatic attraction by an electric charge, intramolecular polarization or the like in the molecule. The anionic substance as the adhesion-competitive agent is a substance exhibiting an anionic nature, however, even if it is an amphoteric substance having both cationic group and anionic group, the relative electronegativity varies depending on the pH, binding to another substance(s) or the like, therefore, the amphoteric substance can be classified into an anionic substance as the case may be.

Examples of the anionic substance include anionic lipid, an anionic surfactant (the same definition as above), an anionic polymer and the like, a protein or a peptide or a nucleic acid, which shows an anionic nature at a pH equal to or greater than an isoelectric point, and the like. Preferred examples thereof include dextran sulfate, sodium dextran sulfate, chondroitin sulfate, sodium chondroitin sulfate, hyaluronic acid, chondroitin, dermatan sulfate, heparan sulfate, heparin, keratan sulfate, dextran fluorescein anionic, and the like. The anionic substances may be used alone, or two or more anionic substances may be used in combination.

Examples of the anionic lipid include phosphatidylserine, phosphatidylglycerol, phosphatidylinositol, phosphatidic acid and the like.

Examples of the anionic polymer include polyaspartic acid, a copolymer of styrene with maleic acid, a copolymer of isopropylacrylamide with acrylpyrrolidone, PEG-modified dendrimer, polylactic acid, polylactic acid polyglycolic acid, polyethylene glycolated polylactic acid, dextran sulfate, sodium dextran sulfate, chondroitin sulfate, sodium chondroitin sulfate, hyaluronic acid, chondroitin, dermatan sulfate, heparan sulfate, heparin, keratan sulfate, dextran fluorescein anionic and the like.

The protein or the peptide which shows an anionic nature at a pH equal to or greater than an isoelectric point is not particularly limited as long as it is a protein or a peptide which shows an anionic nature at a pH equal to or greater than the isoelectric point of the substance. Examples thereof include albumin, orosomucoid, globulin, fibrinogen, histone, protamine, ribonuclease, lysozyme and the like.

Examples of the nucleic acid as an anionic substance include DNA, RNA, plasmid, siRNA, ODN and the like. It may have any length and any sequence as long as it does not exhibit a physiological activity.

The adhesion-competitive agent is preferably electrostatically adhered to the lead particles, and is preferably a substance with a size which does not allow the crosslinking formation to aggregate the lead particles even if the substance is adhered to the lead particles, or a substance having in its molecule, a moiety which is adhered to the lead particles and a moiety which repels the adhesion and suppresses the aggregation of the lead particles.

More specifically, the step 1 can be carried out, for example, in a production method including a step of producing a liquid in which lead particles containing an aggregation-suppressing substance are dispersed, and a step of dispersing or dissolving the RNA so as to be contained in the liquid in which the lead particles are dispersed (for example, a step of adding the RNA to the liquid in which the lead particles are dispersed and dispersing or dissolving the RNA therein, a step of adding a liquid in which the RNA is dispersed or dissolved to the liquid in which the lead particles are dispersed or the like). Here, specific examples of the complex particles obtained by the step of dispersing or dissolving the RNA so as to be contained in the liquid in which the lead particles are dispersed, contain complex particles formed by adhering the RNA to fine particles containing as a constituent component, liposome B containing the cationic lipid, complex particles formed by adhering the RNA to fine particles containing as a constituent component, a lipid assembly containing the cationic lipid, and complex particles formed by adhering the RNA to fine particles containing as a constituent component, a polymer containing a cationic polymer such as poly-L-lysine. Further, the step of dispersing or dissolving the RNA so as to be contained in the liquid in which the lead particles are dispersed is preferably a step of further incorporating the adhesion-competitive agent in the liquid in which the RNA is dispersed or dissolved and adding the resulting liquid to the liquid in which the lead particles are dispersed. In this case, the complex particles are produced by adhering both of the RNA and the adhesion-competitive agent to the lead particles, and the production can be carried out by further suppressing aggregation of the lead particles during the production of the complex particles and aggregation of the complex particles after the production.

The ratio of the lead particles to the liquid in which the lead particles are dispersed is not particularly limited as long as the RNA can be adhered to the lead particles, however, it is preferably about 1 µg/mL to 1 g/mL, more preferably about 0.1 to 500 mg/mL.

Step 2) Step of Coating Complex Particles with Lipid Bilayer Membrane (1)

Lipid particle A can be produced by, for example, a production method including a step of preparing a liquid (liquid A) containing a polar organic solvent in which the complex particles obtained in the step 1 are dispersed and the constituent components of the lipid bilayer membrane are dissolved, and a step of coating the complex particles with the lipid bilayer membrane by reducing the ratio of the polar organic solvent in the liquid A. In this case, the lipid particle A is obtained in the form of a dispersion (liquid B). The solvent in the liquid A is a solvent which contains a polar organic solvent at such a concentration that the constituent components of the lipid bilayer membrane are soluble and the complex particles are dispersible. In the liquid B in which the ratio of the polar organic solvent to the liquid A is reduced, the constituent components of the lipid bilayer membrane are dispersible and the complex particles are also dispersible. In the case where the solvent in the liquid A is a liquid mixture of a polar organic solvent and a solvent different from a polar organic solvent, for example, by adding a solvent containing a solvent different from a polar organic solvent mixable with the polar organic solvent (liquid C), and/or selectively removing the polar organic solvent by distillation by evaporation, semipermeable membrane separation, fractional distillation or the like, the ratio of the polar organic solvent can be reduced. Here, the liquid C is preferably a solvent containing a solvent different from a polar organic solvent, and may also contain a polar organic solvent as long as the ratio of the polar organic solvent in liquid C is lower than that of the polar organic solvent contained in the liquid A.

Examples of the solvent different from a polar organic solvent in the step 2 include water, liquid carbon dioxide, a liquid hydrocarbon, a halogenated carbon, a halogenated hydrocarbon and the like, and preferred examples thereof include water. Further, the liquid A and the liquid C may contain an ion, a buffer component or the like. These may be used alone, or two or more may be used in combination.

The combination of a polar organic solvent with a solvent different from a polar organic solvent is preferably a combination of solvents that are mixable with each other and can be selected by considering the solubility of the complex particles and the constituent components of the lipid bilayer membrane in the solvents in the liquid A and the liquid B, and the liquid C. The complex particles preferably have a low solubility in any of the solvents in the liquid A and the liquid B, and the liquid C, and also preferably have a low solubility in any of a polar organic solvent and a solvent different from a polar organic solvent. The constituent components of the lipid bilayer membrane preferably have a low solubility in the solvent in the liquid B, and the liquid C, and preferably have a high solubility in the solvent in the liquid A, and preferably have a high solubility in a polar organic solvent and preferably have a low solubility in a solvent different from a polar organic solvent. Here, the complex particles having a low solubility means that the elution of each component contained in the complex particles such as the lead particles, RNA and adhesion-competitive agent in the solvent is low, and even if the respective solubility of the components are high, it is sufficient that the elution of each component becomes low due to the binding or the like between the respective components. For example, even in the case where the solubility of any of the components contained in the lead particles in the solvent in the liquid A is high, if the lead particles have a positive electric charge, and an electrostatic bond is formed due to an electric charge, intramolecular polarization or the like in the RNA, and the solubility of the component(s) in the solvent in the liquid A becomes low, the elution of the components in the complex particles is suppressed, whereby the solubility of the complex particles in the solvent in the liquid A can be lowered. That is, if the lead particles have a positive electric charge, the elution of the components of the complex particles is suppressed in the production of the lipid particle A, and an effect of improving the productivity and yield is imparted.

The concentration of the polar organic solvent in the liquid A is not particularly limited as long as it is a concentration at which the constituent components of the lipid bilayer membrane are soluble and the complex particles are dispersible, and varies depending on the solvent or the complex particles to be used, the type of constituent components of the lipid bilayer membrane or the like. However, it is preferably about 30 v/v % or more, more preferably 60 to 90 v/v %. Further, the concentration of the polar organic solvent in the liquid B is not particularly limited as long as the liquid B contains the polar organic solvent at a concentration lower than the liquid A and it is a concentration at which the constituent components of the lipid bilayer membrane are dispersible and the complex particles are also dispersible, however, it is preferably about 50 v/v % or less.

The step of preparing the liquid A may be a step of preparing the liquid A by adding the polar organic solvent, the complex particles and the constituent components of the lipid bilayer membrane, further the solvent different from the polar organic solvent, if necessary. The polar organic solvent, the complex particles, the constituent components of the lipid bilayer membrane and the solvent different from the polar organic solvent can be added in any order as long as the complex particles are not dissolved. Preferably, a step of preparing the liquid A by preparing a liquid (liquid D) containing a polar organic solvent in which the complex particles are dispersed, preparing a liquid (liquid E) in which the constituent components of the lipid bilayer membrane are dissolved in a solvent containing a polar organic solvent that is the same as or different from the polar organic solvent in the liquid D and mixing the liquid D and the liquid E can be exemplified. When the liquid A is prepared by mixing the liquid D and the liquid E, it is preferred to mix them gradually.

Step 3) Step of Coating Complex Particles with Lipid Bilayer Membrane (2)

Lipid particle A can be produced by a production method including a step of dispersing the complex particles obtained in the step 1 and the constituent components of the lipid bilayer membrane in a liquid (liquid F) which contains a polar organic solvent in which the constituent components of the lipid bilayer membrane are soluble at a concentration at which the constituent components of the lipid bilayer membrane are present in a dispersed state. In this case, the lipid particle A can be obtained in a state of a dispersion. Although the constituent components of the lipid bilayer membrane are soluble in a polar organic solvent contained in liquid F, liquid F contains the polar organic solvent, wherein the polar organic solvent can be contained in liquid F at such a concentration that the constituent components of the lipid bilayer membrane are dispersible and the complex particles are dispersible.

As a method of preparing the liquid F, any embodiment can be employed. For example, the liquid F may be prepared by preparing a dispersion of complex particles and a solution or a dispersion of the constituent components of the lipid bilayer membrane and mixing both liquids, or the liquid F may be prepared by preparing either one of the dispersions of the complex particles and the constituent components of the lipid bilayer membrane, and adding and dispersing the other remaining complex particles or constituent components of the lipid bilayer membrane in the form of a solid in the resulting dispersion. In the case where a dispersion of the complex particles and a solution or a dispersion of the constituent components of the lipid bilayer membrane are mixed, a dispersion medium of the complex particles may contain a polar organic solvent in advance, and a solvent or a dispersion medium of the constituent components of the lipid bilayer membrane may be a liquid containing a polar organic solvent or a liquid composed only of a polar organic solvent. On the other hand, in the case where the dispersions of either one of the complex particles and the constituent components of the lipid bilayer membrane is prepared, and the other remaining complex particles or constituent components of the lipid bilayer membrane in the form of a solid are added to the resulting dispersion, the resulting dispersion is preferably a liquid containing a polar organic solvent. Incidentally, in the case where the complex particles are not dissolved and the constituent components of the lipid bilayer membrane are dispersed after the liquid F is prepared, a polar organic solvent may be added in a concentration range of the polar organic solvent in which the complex particles are not dissolved and the constituent components of the lipid bilayer membrane are dispersed, or the organic solvent may be removed or the concentration thereof may be reduced. On the other hand, in the case where the complex particles are not dissolved and the constituent components of the lipid bilayer membrane are dissolved after the liquid F is prepared, the polar organic solvent may be removed or the concentration thereof may be reduced in a concentration range of the polar organic solvent in which the complex particles are not dissolved and the constituent components of the lipid bilayer membrane are dispersed. Alternatively, the complex particles and the constituent components of the lipid bilayer membrane are mixed in a solvent different from a polar organic solvent in advance, and a polar organic solvent may be added thereto in a concentration range of the polar organic solvent in which the complex particles are not dissolved and the constituent components of the lipid bilayer membrane are dispersed. In this case, the complex particles and the constituent components of the lipid bilayer membrane are separately dispersed in solvents different from a polar organic solvent, and both dispersions are mixed, and then, a polar organic solvent may be added thereto, or either one of the complex particles and the constituent components of the lipid bilayer membrane are dispersed in a solvent different from a polar organic solvent, and the other remaining complex particles or constituent components of the lipid bilayer membrane in the form of a solid are added to the resulting dispersion, and then a polar organic solvent may be added thereto. Further, it is preferred to include a step of letting a liquid, in which the complex particles and the constituent components of the lipid bilayer membrane are dispersed and a polar organic solvent is contained, stand or mixing the liquid for a time sufficient to coat the complex particles with the lipid bilayer membrane. The time for letting the liquid stand or mixing the liquid after the complex particles and the constituent components of the lipid bilayer membrane are dispersed in the liquid containing the polar organic solvent is not limited as long as it is not completed immediately after the complex particles and the constituent components of the lipid bilayer membrane are dispersed in the liquid containing the polar organic solvent, however, it can arbitrarily be set depending on the constituent components of the lipid bilayer membrane or the type of the liquid containing the polar organic solvent, and it is preferably to set to a time which keeps the yield of the obtained lipid particle A constant, for example, 3 seconds to 30 minutes.

Examples of the solvent different from a polar organic solvent in the liquid F include those illustrated in the solvent different from a polar organic solvent in the step 2, and preferred examples thereof contain water.

The concentration of the polar organic solvent in the liquid F is not particularly limited as long as only the requirement that both of the complex particles and the constituent components of the lipid bilayer membrane are dispersed is met, and varies depending on the solvent or the complex particles to be used, the type of the constituent components of the lipid bilayer membrane or the like. However, it is preferably about 1 to 80 vol %, more preferably about 10 to 60 vol %, more preferably about 20 to 50 vol %, and the most preferably about 30 to 40 vol %.

In the present invention, the description of the constituent components of the lipid bilayer membrane being soluble in a polar organic solvent include a case in which the constituent components of the lipid bilayer membrane have a property of being dissolved in a polar organic solvent, a case in which the constituent components of the lipid bilayer membrane have a property of being dissolved in a polar organic solvent with the help of a solubilizer or the like, a case in which the constituent components of the lipid bilayer membrane have a property capable of being emulsified or formed into an emulsion by forming aggregates, micelles or the like in a polar organic solvent and the like. Further, the description of the constituent components of the lipid bilayer membrane being dispersible includes a state in which the whole of the constituent components of the lipid bilayer membrane form aggregates, micelles or the like and are emulsified or formed into an emulsion, a state in which a part of the constituent components of the lipid bilayer membrane form aggregates, micelles or the like and are emulsified or formed into an emulsion, and the rest of the components are dissolved, a state in which a part of the constituent components of the lipid bilayer membrane form aggregates, micelles or the like and are emulsified or formed into an emulsion, and the rest of the components are precipitated and the like. Incidentally, the description of the constituent components of the lipid bilayer membrane being dissolved does not include a state in which the whole of the constituent components of the lipid bilayer membrane form aggregates, micelles or the like and are emulsified or formed into an emulsion.

In the present invention, the description of the complex particles being dispersed means a state in which the complex particles are suspended or emulsified or formed into an emulsion, and includes a state in which a part of the complex particles are suspended or emulsified or formed into an emulsion, and the rest of the particles are dissolved, a state in which a part of the complex particles are emulsified or formed into an emulsion, and the rest of the particles are precipitated and the like. The description of the complex particles being not dissolved is the same as the above-mentioned definition of the complex particles being dispersed.

The concentration of the complex particles in the aqueous solution containing a polar organic solvent to be used in the method of producing lipid particle A according to the present invention is not particularly limited, as long as it allows the complex particles to be coated with the lipid bilayer membrane, however, it is preferably about 1 μg/mL to 1 g/mL, more preferably about 0.1 to 500 mg/mL. Further, the concentration of the constituent components of the lipid bilayer membrane to be used is not particularly limited as long as it allows the complex particles to be coated, however, it is preferably about 1 μg/mL to 1 g/mL, more preferably about 0.1 to 400 mg/mL.

The ratio of the lipid bilayer membrane to the lipid particle A of the present invention is preferably about 1:0.1 to 1:1000, more preferably about 1:1 to 1:10 in ratio by weight.

Further, as for the size of the lipid particle A of the present invention, an average particles diameter is preferably about 300 nm or less, more preferably about 200 nm or less. Specifically, for example, an injectable size is preferred.

Further, the lipid particle A obtained above can be modified with a substance such as a protein including an antibody and the like, a saccharide, a glycolipid, an amino acid, a nucleic acid, or any of various low-molecular compounds and polymers, and such coated complex particles obtained by modification is included in the lipid particle A. For example, in order to apply to targeting, it is possible that the lipid particle A obtained above is further subjected to a surface modification of the lipid bilayer membrane using a protein such as an antibody, a peptide, a fatty acid or the like [see *Stealth Liposomes*, edited by D. D. Lasic and F. Martin, CRC Press Inc., USA, pp. 93-102, (1995)]. Further, surface improvement can also be optionally carried out to the lipid particle A using, for example, a lipid derivative, a fatty acid derivative, or an aliphatic hydrocarbon derivative of a water-soluble substance. The lipid derivative, the fatty acid derivative, and the aliphatic hydrocarbon derivative of a water-soluble substance to be used in the surface modification have the same definitions as the lipid derivative, the fatty acid derivative, and the aliphatic hydrocarbon derivative of a water-soluble substance as the constituent components of the lipid bilayer membrane.

By administering the composition of the present invention to a mammal including humans, the RNA can be delivered to an expression site of a target gene, and, for example, an RNA capable of suppressing the expression of the gene can be introduced into a mammalian cell in vivo, making it possible to suppress expression of the gene or the like. For example, when the target gene of the composition of the present invention is a gene associated with tumor or inflammation, the composition of the present invention can be used as a therapeutic or preventive agent for cancer or inflammatory disease, preferably a therapeutic or preventive agent for solid cancer, or inflammation in blood vessels or in the vicinity of blood vessels. Specifically, for example, when the target gene of the composition of the present invention is a gene associated with angiogenesis or the like, the growth of the vascular smooth muscle, angiogenesis, or the like can be suppressed, and the composition of the present invention can be used, for example, as a therapeutic or preventive agent for cancer or inflammatory disease involving growth of the vascular smooth muscle or angiogenesis.

In other words, the present invention also provides a method for treating cancer or inflammatory disease, by which the composition of the present invention described above is administered to a mammal. Preferably the subject of administration is human, preferably human individuals affected by cancer or inflammatory disease.

Further, the composition of the present invention can also be used as a tool for acquiring POC (proof of concept) in an in vivo screening system concerning a therapeutic or preventive agent for cancer or inflammatory disease.

The composition of the present invention can be used as a preparation intended for stabilization of the RNA in a living body component such as a blood component (for example, blood, gastrointestinal tract or the like), reduction of side effects, increase in drug accumulation in tissues or organs containing the expression site of the target gene, and the like.

In the case where the composition of the present invention is used as a therapeutic or preventive agent for diseases such as cancer and inflammation, it is preferred that an administration route that is most effective for treatment be used. Examples of the administration route include parenteral administration routes such as intraoral administration, tracheobronchial administration, intrarectal administration, subcutaneous administration, intramuscular administration, and intravenous administration, and oral administration routes. Preferred examples thereof include intravenous administration and intramuscular administration, and more preferred examples thereof include intravenous administration.

The doses may vary depending upon conditions and age of the subject, administration route, and the like. For example, a dose of about 0.1 μg to 1000 mg in terms of RNA is administered daily.

As a preparation suitable for intravenous administration or intramuscular administration, for example, an injection can be exemplified, and it is also possible to use the dispersion of the lipid particle A prepared by the above-mentioned method as it is in the form of, for example, an injection or the like. However, it can also be used after removing the solvent from the dispersion by, for example, filtration, centrifugation or the like, or after lyophilizing the dispersion or the dispersion supplemented with an excipient such as mannitol, lactose, trehalose, maltose or glycine.

In the case of an injection, it is preferred that an injection is prepared by mixing, for example, water, an acid, an alkali, any of various buffers, a physiological saline solution, an amino acid infusion or the like with the dispersion of the lipid particle A or the lipid particle A obtained by removing the solvent or lyophilization. Further, it is possible to prepare an injection by adding an antioxidant such as citric acid, ascorbic acid, cysteine or EDTA, an isotonic agent such as glycerol, glucose or sodium chloride or the like. Further, it can also be cryopreserved by adding a cryopreservation agent such as glycerol.

Among the compositions of the present invention described above, the therapeutic agent for cancer or inflammatory disease of the present invention may be a composition that includes:

an RNA that contains a sequence consisting of 15 to 30 contiguous bases of mRNA of a target gene associated with tumor or inflammation (hereinafter, sequence $X_1$), and a base sequence (hereinafter, complementary sequence $X_1'$) complementary to the sequence $X_1$, 1 to 90% of all sugars binding to the bases of sequence $X_1$ and complementary sequence $X_1'$ being ribose that has a substitution by a modifying group at 2' position; and lipid particle A which may be either a lipid particle including a complex particle that contains a lead particle and the RNA as constituent components, and a lipid bilayer membrane for coating the complex particle, the constituent components of the lipid bilayer membrane being soluble in a polar organic solvent, and the constituent components of the lipid bilayer membrane and the complex particle being dispersible in a liquid that contain the polar organic solvent in a specific concentration, or a lipid particle including a complex particle that contains a cationic substance-containing lead particle and the RNA as constituent components, and a lipid bilayer membrane for coating the complex particle, the lipid bilayer membrane containing, as constituent components, a neutral lipid, and a lipid derivative, a fatty acid derivative, or an aliphatic hydrocarbon derivative of a water-soluble substance. In the therapeutic agent for cancer or inflammatory disease of the present invention, the cancer is preferably a solid cancer, and the inflammatory disease is preferably inflammation in blood vessels or in the vicinity of blood vessels.

Further, the present invention provides use of the composition of the present invention described above for the manufacture of a therapeutic agent for cancer or inflammatory disease, preferably a therapeutic agent for solid cancer, or inflammation in blood vessels or in the vicinity of blood vessels. The composition may be a composition that includes:

an RNA that contains a sequence consisting of 15 to 30 contiguous bases of mRNA of a target gene associated with tumor or inflammation (hereinafter, sequence $X_1$), and a base sequence (hereinafter, complementary sequence $X_1'$) complementary to the sequence $X_1$, 1 to 90% of all sugars binding to the bases of sequence $X_1$ and complementary sequence $X_1'$ being ribose that has a substitution by a modifying group at 2' position; and lipid particle A which may be either a lipid particle including a complex particle that contains a lead particle and the RNA as constituent components, and a lipid bilayer membrane for coating the complex particle, the constituent components of the lipid bilayer membrane being soluble in a polar organic solvent, and the constituent components of the lipid bilayer membrane and the complex particle being dispersible in a liquid that contain the polar organic solvent in a specific concentration, or a lipid particle including a complex particle that contains a cationic substance-containing lead particle and the RNA as constituent components, and a lipid bilayer membrane for coating the complex particle, the lipid bilayer membrane containing, as constituent components, a neutral lipid, and a lipid derivative, a fatty acid derivative, or an aliphatic hydrocarbon derivative of a water-soluble substance.

The present invention will be specifically described below with reference to Examples and Test examples. However, the present invention is not limited to these Examples and Test examples.

Example 1

The RNA used in Example 1 is a double-stranded RNA that contains a sequence consisting of 19 contiguous bases of a BCL2 gene mRNA (hereinafter, sequence $X_2$) and a base sequence (hereinafter, sequence $X_2'$) complementary to sequence $X_2$ [sense: 5'-GmUG mAAmG UmCA mACmA UmGC mCUmG CdTdT-3' (the sugars binding to the bases prefaced by d are deoxyriboses, and the sugars binding to the 2nd, 4th, 6th, 8th, 10th, 12th, 14th, 16th, and 18th bases prefaced by m relative to the 5'-end are 2'-O-methyl-substituted riboses) (SEQ ID NO: 1); antisense: 5'-mGCmA GmGC mAUmG UmUG mACmU UmCA mCdTdT-3' (the sugars binding to the bases prefaced by d are deoxyriboses, and the sugars binding to the 1st, 3rd, 5th, 7th, 9th, 11th, 13th, 15th, 17th, and 19th bases prefaced by m relative to the 5'-end are 2'-O-methyl-substituted riboses) (SEQ ID NO: 2)] (hereinafter, 2'-OMe BCL2siRNA Exp.1). Fifty percent of all riboses binding to the bases of sequence $X_2$ and complementary sequence $X_2'$ are riboses substituted with a 2'-O-methyl group. The sense strand and antisense strand were obtained from Eurogentec (Belgium), and were annealed to prepare the double-stranded RNA.

DOTAP (manufactured by Avanti Polar Lipids Inc.), PEG-DSPE (manufactured by NOF Corporation) and distilled water (manufactured by Otsuka Pharmaceutical Co., Ltd.) were mixed such that the ratio of DOTAP/PEG-DSPE/distilled water was 40 mg/16 mg/1 mL, and the mixture was stirred by shaking with a vortex mixer. The obtained suspension was passed, at 70° C., through a 0.4-μm polycarbonate membrane filter (manufactured by Costar) 10 times and through a 0.2-μm polycarbonate membrane filter (manufactured by Whatman) 3 times and then through a 0.1-μm polycarbonate membrane filter (manufactured by Corning) 10 times and a 0.05-μm polycarbonate membrane filter (manufactured by Whatman) 20 times. The lead particle had an average particles diameter of 73.01 nm as measured by Dynamic light scattering (DLS).

Separately, EPC(NOF Corporation)/PEG-DSPE (NOF Corporation)/ethanol (Wako Pure Chemical Industries, Ltd.)/water (15 mg/3.125 mg/0.625 mL/0.375 mL) were mixed, and a solution containing the constituent components of the lipid bilayer membrane was prepared.

The obtained lead particle dispersion (0.875 mL) was mixed with an aqueous solution (0.2917 mL) obtained by mixing 2'-OMe BCL2siRNA Exp.1 in water in a proportion of 24 mg/1 mL, so as to prepare the complex particles. The obtained dispersion of complex particles was added to the solution of lipid bilayer membrane constituent components (4.667 mL), and 1.459 mL of distilled water was added. Then, after adding the solution of lipid bilayer membrane constituent components (0.4667 mL), distilled water (54.31 mL) was gradually added to adjust the ethanol concentration to 5% or less. The obtained lipid particle suspension was subjected to ultracentrifugation (80 min, 110,000×g, 25° C.), and the supernatant was removed. The precipitate was resuspended in about 5 mL of physiological saline (Otsuka Pharmaceutical Co., Ltd.).

The lipid particle had an average particles diameter of 92.89 nm as measured by DLS. Quantification of 2'-OMe BCL2siRNA Exp.1 in the lipid particle found that the concentration was 1.2460 mg/mL, and that the percentage recovery with respect to the charged amount of 2'-OMe BCL2siRNA Exp.1 was 88.02%. Finally, a preparation was obtained by adjusting the 2'-OMe BCL2siRNA Exp.1 concentration to 0.75 mg/mL with addition of physiological saline (3.270 mL).

Comparative Example 1

The RNA used in Comparative Example 1 is a double-stranded RNA that contains sequence $X_2$ and complementary sequence $X_2$' [sense: 5'-GUG AAG UCA ACA UGC CUG CdTdT-3' (the sugars binding to the bases prefaced by d are deoxyriboses) (SEQ ID NO: 3); antisense: 5'-GCA GGC AUG UUG ACU UCA CdTdT-3' (the sugars binding to the bases prefaced by d are deoxyriboses) (SEQ ID NO: 4)] (hereinafter, BCL2siRNA Com.1). The sense strand and antisense strand were obtained from Eurogentec (Belgium), and were annealed to prepare the double-stranded RNA.

The complex particles were prepared by mixing a 24 mg/mL aqueous solution of BCL2siRNA Com.1 (0.1667 mL) with a dispersion of lead particle (0.5 mL) obtained in the same manner as in Example 1. The obtained dispersion of complex particles was added to a solution of lipid bilayer membrane constituent components (2.667 mL), and distilled water (0.8334 mL) was added. Then, after adding the solution of lipid bilayer membrane constituent component (0.2667 mL), distilled water (31.03 mL) was gradually added to adjust the ethanol concentration to 5% or less. The obtained lipid particle suspension was subjected to ultracentrifugation (80 min, 110,000×g, 25° C.), and the supernatant was removed. The precipitate was resuspended in about 2 mL of physiological saline (Otsuka Pharmaceutical Co., Ltd.).

The lipid particle had an average particles diameter of 88.31 nm as measured by DLS. Quantification of BCL2siRNA Com.1 in the lipid particle found that the concentration was 1.7332 mg/mL, and that the percentage recovery with respect to the charged amount of BCL2siRNA Com.1 was 90.09%. Finally, a preparation was obtained by adjusting the BCL2siRNA Com.1 concentration to 1.5 mg/mL with addition of physiological saline (0.3232 mL).

Test Example 1

Drug solutions (siRNA concentration, 750 μg/mL; 200 μL) containing the preparations obtained in Example 1 and Comparative Example 1 were administered twice to male Balb/c mice (6 weeks of age, CLEA Japan, Inc.) through the tail vein at the 7-day interval (dose, 150 μg/mouse). After the second administration, blood (10 μL) was collected from the tail artery at each time point after 0.5, 3, 7, and 24 hours, and mixed with 90 μL of a denaturing solution (4 mol/L guanidine thiocyanate, 25 mmol/L sodium citrate, 0.1 v/v % 2-mercaptoethanol, 0.5 w/v % sodium N-lauroyl sarcosine; hereinafter, D solution). As a result, a 10 v/v % blood was obtained.

The 10 v/v % blood (10 μL) of the group to which the preparation obtained in Example 1 was mixed with 10 μL of a diethylpyrocarbonate aqueous solution (a 0.1 v/v % mixture of diethylpyrocarbonate in ultrapure water), 10 μL of I.S. solution (0.3 μmol/L of the diethylpyrocarbonate aqueous solution as I.S.), 100 μL of D solution, 10 μL of 2 mmol/L sodium acetate (pH 4.0), and 150 pit of a TE (10 mM Tris-HCl, pH 8.0, 1 mM EDTA) saturated phenol/chloroform solution (the lower layer of a 1:1 volume ratio mixture of TE-saturated phenol and chloroform was used). The mixture was then centrifuged at 132,000×g for 10 min at 4° C. The supernatant (65 μL) was mixed with 15 μL of a GenTLE solution (GenTLE precipitation carrier (Takara Bio Inc.) diluted 15 times with the diethylpyrocarbonate aqueous solution), and the mixture was allowed to stand at room temperature for at least 10 min after addition of ethanol (200 μl). After 10-min centrifugation (132,000×g) at 4° C., the supernatant was discarded, and 75 v/v % ethanol (200 μL) was added to the precipitate. After 15-min centrifugation (132,000×g) at 4° C., the supernatant was discarded, and the precipitate was air-dried and dissolved in 100 μL of a redissolving solution (a 0.1/0.4/30/1,000 volume ratio mixture of diethylpyrocarbonate/triethylamine/hexafluoroisopropanol/water). The mixture was centrifuged at 132,000×g for 10 min at 4° C., and the supernatant as an analysis sample was quantified using HPLC. The results are shown in FIG. 1.

Apparatus
HPLC apparatus: ACQUITY HPLC System (Waters)
Mass spectroscope: API4000 Q TRAP (Applied Biosystems/MDS Sciex)
Analysis software: Analyst 1.4.2 (Applied Biosystems/MDS Sciex)

HPLC Conditions
Internal Standard Substance (I.S.)
5'-GmUG mAAmG UmCA mACmA UmGC mCUmG CdT-3' (the sugar binding to the base prefaced by d is deoxyriboses, and the sugars binding to the 2nd, 4th, 6th, 8th, 10th, 12th, 14th, 16th, and 18th bases prefaced by m relative to the 5'-end are 2'-O-methyl-substituted riboses) (SEQ ID NO: 5)
5'-mGCmA GmGC mAUmG UmUG mACmU UmCA mCdT-3' (the sugar binding to the base prefaced by d is deoxyriboses, and the sugars binding to the 1st, 3rd, 5th, 7th, 9th, 11th, 13th, 15th, 17th, and 19th bases prefaced by m relative to the 5'-end are 2'-O-methyl-substituted riboses) (SEQ ID NO: 6)
Column: Xbridge C18 (3.5 μm, 2.1 mm I.D.×50 mm, Waters)
Prefilter: Xbridge guard cartridge (3.5 μm, 2.1 mm I.D.×10 mm, Waters)
Column temperature: 65° C.
Mobile phase: triethylamine/hexafluoroisopropanol/water (0.4/30/1000):methanol=93:7 to 75:25
Injection amount: 25 μL,
Detection: Mass spectroscope (ionization method: electrospray ionization, negative, ion source temperature: 500° C.)

Figure 2:
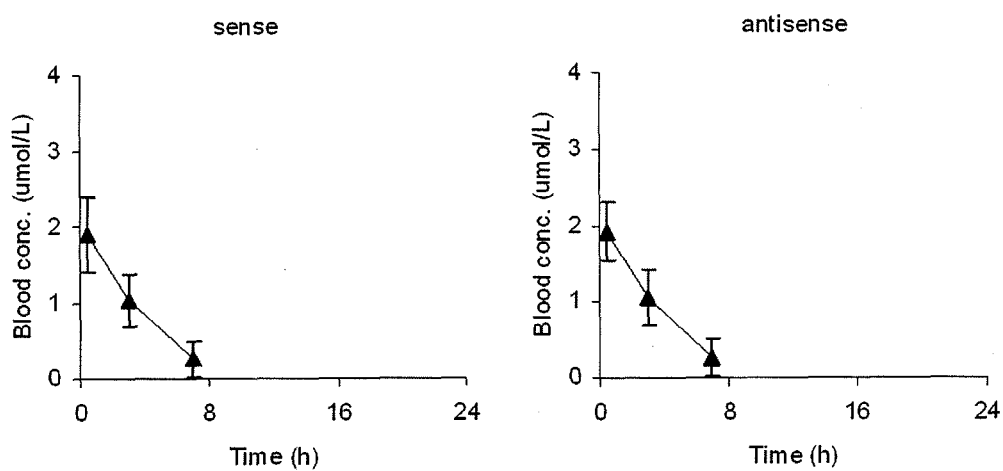
FIG. 2 shows blood RNA concentrations in response to administration of a preparation obtained in Comparative Example 1; the horizontal axis represents time (hours) after administration of the preparation; the vertical axis represents blood RNA concentration (μmol/L).

The 10 v/v % blood (10 μL) of the group to which the preparation obtained in Comparative Example 1 was mixed with 10 μL of a diethylpyrocarbonate aqueous solution (a 0.1 v/v % mixture of diethylpyrocarbonate in ultrapure water), 10 μL of I.S. solution (0.3 μmol/L, of the diethylpyrocarbonate aqueous solution as 100 μL of D solution, 10 μL of 2 mmol/L sodium acetate (pH 4.0), and 150 μL of an acidic saturated phenol/chloroform solution (the lower layer of a 1:1 volume ratio mixture of acidic saturated phenol and chloroform was used). The mixture was then centrifuged at 132,000×g for 10 min at 4° C. The supernatant (65 µL) was mixed with 15 µL of a GenTLE solution (GenTLE precipitation carrier (Takara Bio Inc.) diluted 15 times with the diethylpyrocarbonate aqueous solution), and the mixture was allowed to stand at room temperature for at least 10 min after addition of ethanol (200 µL). After 10-min centrifugation (132,000×g) at 4° C., the supernatant was discarded, and 75 v/v % ethanol (200 µL) was added to the precipitate. After 15-min centrifugation (132,000×g) at 4° C., the supernatant was discarded, and the precipitate was air-dried and dissolved in 100 µL of a redissolving solution (a 0.1/0.4/30/1,000 volume ratio mixture of diethylpyrocarbonate/triethylamine/hexafluoroisopropanol/water). The mixture was centrifuged at 132,000×g for 10 min at 4° C., and the supernatant as an analysis sample was quantified using HPLC. The results are shown in FIG. 2.

Apparatus
HPLC apparatus: ACQUITY HPLC System (Waters)
Mass spectroscope: API4000 Q TRAP (Applied Biosystems/MDS Sciex)
Analysis software: Analyst 1.4.2 (Applied Biosystems/MDS Sciex)
HPLC Conditions
Internal Standard Substance (I.S.)
5'-GUG AAG UCA ACA UGC CUG dTdT-3' (the sugars binding the bases prefaced by d are deoxyriboses) (SEQ ID NO: 7)
5'-CAG GCA UGU UGA CUU CAC dTdT-3' (the sugars binding to the bases prefaced by d are deoxyriboses) (SEQ ID NO: 8)
Column: Xbridge C18 (3.5 µm, 2.1 mm I.D.×50 mm, Waters)
Prefilter: Xbridge guard cartridge (3.5 µm, 2.1 mm I.D.×10 mm, Waters)
Column temperature: 65° C.
Mobile phase: triethylamine/hexafluoroisopropanol/water (0.4/30/1000):methanol=93:7 to 75:25
Injection amount: 25 µL
Detection: Mass spectroscope (ionization method: electrospray ionization, negative, ion source temperature: 500° C.)

The present invention also provides an easy and accurate method for measuring a blood siRNA concentration. The method for measuring a blood siRNA concentration of the present invention may be a method in which, as specifically described in Test Example 1, the siRNA in a test solution, preferably in the presence of the IS nucleic acid having different numbers of bases from those of the siRNA being measured, is formed into an electrically neutral complex by addition of a reagent, for example, GenTLE solution, that forms a complex with nucleic acid, and in which the complex is separated, then dissolved in a redissolving solution, and the resulting solution is analyzed by high-performance liquid chromatography to measure the siRNA concentration.

Note that the measurement of blood siRNA concentration is not limited to the method for measuring a blood siRNA concentration of the present invention, and the blood siRNA concentration may be measured according to an ordinary method.

FIGS. 1 and 2 show that the transition of blood RNA concentration is higher in the mice to which the preparation of Example 1 was administered than in the mice to which the preparation of Comparative Example 1 was administered. Specifically, the composition of the present invention in which 1 to 90% of all sugars binding to the bases of sequence X and complementary sequence X' are riboses substituted by a modifying group at 2' position was found to have improved retention in the blood, reduced side effects, or enhanced drug accumulation in tissues or organs containing the expression site of the target gene.

Example 2

The RNA used in Example 2 is a double-stranded RNA containing a sequence consisting of 19 contiguous bases of a BCL2 gene mRNA (hereinafter, sequence $X_3$), and a base sequence (hereinafter, complementary sequence $X_3$') complementary to sequence $X_3$ [sense: 5'-GmAA mGUmG AmCA mUCmU UmCA mGCmA AdTdT-3' (the sugars binding the bases prefaced by d are deoxyriboses, and the sugars binding to the 2nd, 4th, 6th, 8th, 10th, 12th, 14th, 16th, and 18th bases prefaced by m relative to the 5'-end are 2'-O-methyl-substituted riboses) (SEQ ID NO: 9); antisense: 5'-mUUmG CmUG mAAmG AmUG mUCmA CmUU mCdTdT-3' (the sugars binding to the bases prefaced by d are deoxyriboses, and the sugars binding to the 1st, 3rd, 5th, 7th, 9th, 11th, 13th, 15th, 17th, and 19th bases prefaced by m relative to the 5'-end are 2'-O-methyl-substituted riboses) (SEQ ID NO: 10)] (hereinafter, 2'-OMe BCL2siRNA Exp.2). Fifty percent of all riboses binding to the base of sequence $X_3$ and complementary sequence $X_3$' are riboses substituted with a 2'-O-methyl group. The sense strand and antisense strand were obtained from Hokkaido System Science Co., Ltd., and were annealed to prepare the double-stranded RNA.

DOTAP (manufactured by Avanti Polar Lipids Inc.), PEG-DSPE (manufactured by NOF Corporation) and distilled water (Otsuka Pharmaceutical Co., Ltd.) were mixed such that the ratio of DOTAP/PEG-DSPE/distilled water was 40 mg/16 mg/1 mL, and the mixture was stirred by shaking with a vortex mixer. The obtained suspension was passed, at 70° C., through a 0.4-µm polycarbonate membrane filter (manufactured by Costar) 10 times and through a 0.2-µm polycarbonate membrane filter (manufactured by Whatman) 3 times and then through a 0.1-µm polycarbonate membrane filter (manufactured by Corning) 10 times and a 0.05-µm polycarbonate membrane filter (manufactured by Whatman) 20 times. The lead particle had an average particles diameter of 70.71 nm as measured by Dynamic light scattering (DLS).

Separately, EPC(NOF Corporation)/PEG-DSPE (NOF Corporation)/ethanol (Wako Pure Chemical Industries, Ltd.)/water (15 mg/3.125 mg/0.625 mL/0.375 mL) were mixed, and a solution containing the constituent components of the lipid bilayer membrane was prepared.

The obtained lead particle dispersion (0.225 mL) was mixed with an aqueous solution (0.075 mL) obtained by mixing 2'-OMe BCL2siRNA Exp.2 in water in a proportion of 24 mg/1 mL, so as to prepare the complex particles. The obtained dispersion of complex particles was then added to the solution of lipid bilayer membrane constituent components (1.2 mL), and 0.375 mL of distilled water was added. Then, after adding 0.12 mL of a solution of EPC/PEG-DSPE (62.5 mg/62.5 mg/mL) in 40 vol % ethanol, distilled water (13.965 mL) was gradually added to adjust the ethanol concentration to 5 vol % or less. The obtained lipid particle suspension was subjected to ultracentrifugation (80 min, 110,000×g, 25° C.), and the supernatant was removed. The precipitate was resuspended in physiological saline (Otsuka Pharmaceutical Co., Ltd.).

The lipid particle had an average particles diameter of 88.52 nm as measured by DLS. Quantification of 2'-OMe BCL2siRNA Exp.2 in the lipid particle found that the concentration was 2.307 mg/mL, and that the percentage recovery with respect to the charged amount of 2'-OMe BCL2siRNA Exp.2 was 87.2%. Finally, a preparation was obtained by adjusting the 2'-OMe BCL2siRNA Exp.2 concentration to 1.5 mg/mL with addition of physiological saline (0.366 mL).

Example 3

The RNA used in Example 3 is a double-stranded RNA containing sequence $X_3$ and complementary sequence $X_3'$ [sense: 5'-GmAA mGUmG AmCA mUCmU UmCA mGCmA AdTdT-3' (the sugars binding to the bases prefaced by d are deoxyriboses, and the sugars binding to the 2nd, 4th, 6th, 8th, 10th, 12th, 14th, 16th, and 18th bases prefaced by m relative to the 5'-end are 2'-O-methyl-substituted riboses) (SEQ ID NO: 11); antisense: 5'-UUG CUG AAG AUG UCA CUU CdTdT-3' (the sugars binding to the bases prefaced by d are deoxyriboses) (SEQ ID NO: 12)](hereinafter, 2'-OMe BCL2siRNA Exp.3). Twenty-four percent of all riboses binding to the bases of the sequence $X_3$ and complementary sequence $X_3'$ are riboses substituted with a 2'-O-methyl group. The sense strand and antisense strand were obtained from Hokkaido System Science Co., Ltd., and were annealed to prepare the double-stranded RNA.

A preparation was obtained in the same manner as in Example 2, except that the 2'-OMe BCL2siRNA Exp.2 was replaced with 2'-OMe BCL2siRNA Exp.3.

The lipid particle had an average particles diameter of 91.42 nm as measured by DLS.

Comparative Example 2

The RNA used in Comparative Example 2 is a double-stranded RNA containing sequence $X_3$ and complementary sequence $X_3'$ [sense: 5'-GAA GUG ACA UCU UCA GCA AdTdT-3' (the sugars binding to the bases prefaced by d are deoxyriboses) (SEQ ID NO: 13); antisense: 5'-UUG CUG AAG AUG UCA CUU CdTdT-3' (the sugars binding to the bases prefaced by d are deoxyriboses) (SEQ ID NO: 14)] (hereinafter, BCL2siRNA Com.2). The sense strand and antisense strand were obtained from Hokkaido System Science Co., Ltd., and were annealed to prepare the double-stranded RNA.

A preparation was obtained in the same manner as in Example 2, except that 2'-OMe BCL2siRNA Exp.2 was replaced with BCL2siRNA Com.2.

The lipid particle had an average particles diameter of 96.52 nm as measured by DLS.

Test Example 2

Drug solutions (siRNA concentration, 750 μg/mL; 200 μL) containing the preparations obtained in Examples 2 and 3 and Comparative Example 2 were administered twice to male Balb/c mice (6 weeks of age, CLEA Japan, Inc.) through the tail vein at the 7-day interval (dose, 150 μg/mouse). After the second administration, blood (10 μL) was collected from the tail artery at each time point after 0.5, 3, 7, and 24 hours, and mixed with 90 μL of a denaturing solution (4 mol/L guanidine thiocyanate, 25 mmol/L sodium citrate, 1 mmol/L dithiothreitol, 0.5 w/v % sodium N-lauroyl sarcosine; hereinafter, D solution). As a result, a 10 v/v % blood was obtained.

Figure 3:
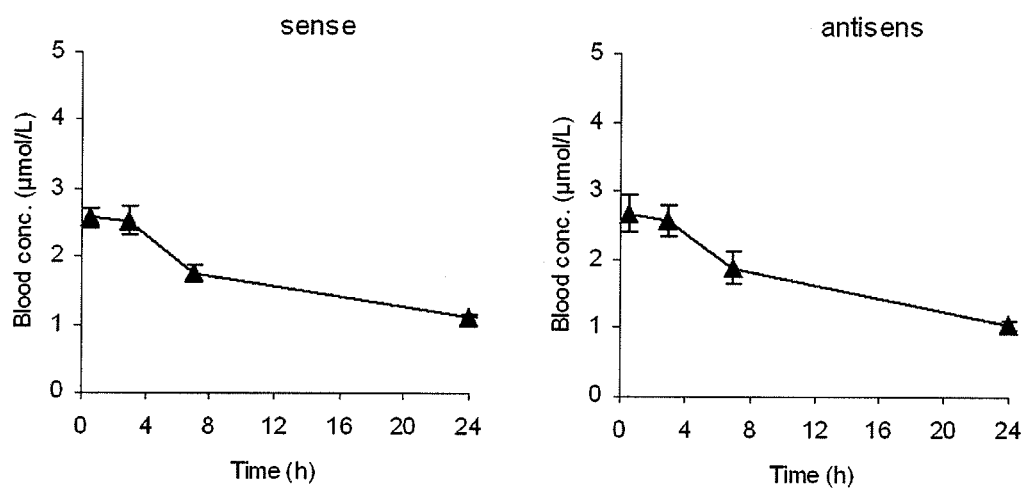
FIG. 3 shows blood RNA concentrations in response to administration of a preparation obtained in Example 2; the horizontal axis represents time (hours) after administration of the preparation; the vertical axis represents blood RNA concentration (μmol/L).
Figure 4:
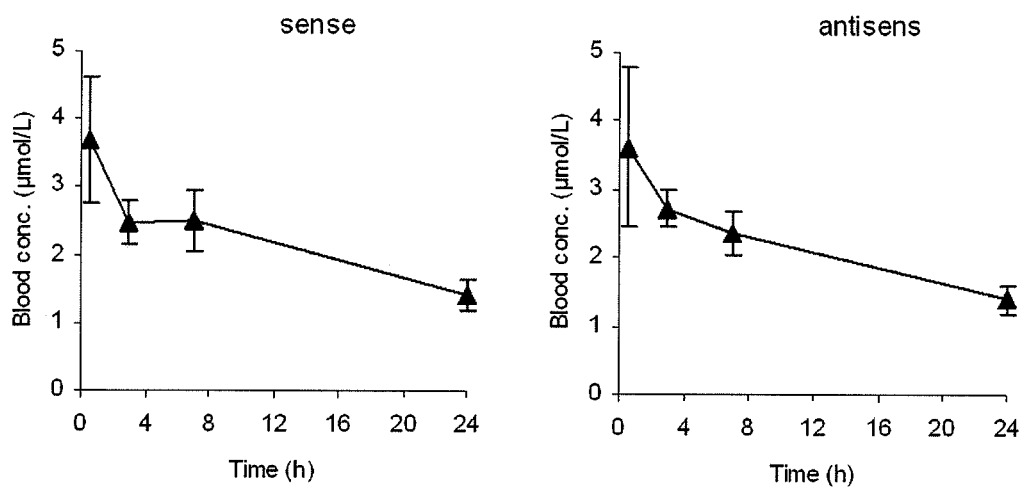
FIG. 4 shows blood RNA concentrations in response to administration of a preparation obtained in Example 3; the horizontal axis represents time (hours) after administration of the preparation; the vertical axis represents blood RNA concentration (μmol/L).
Figure 5:
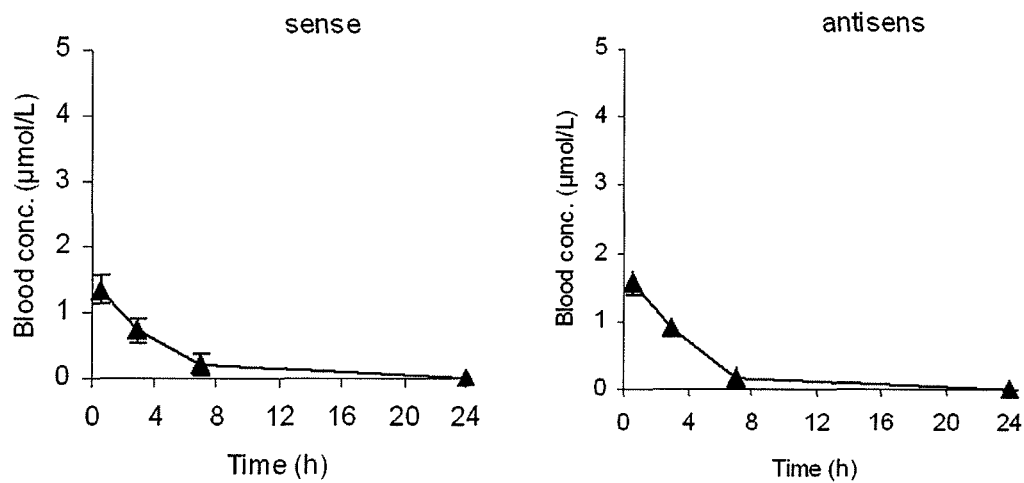
FIG. 5 shows blood RNA concentrations in response to administration of a preparation obtained in Comparative Example 2; the horizontal axis represents time (hours) after administration of the preparation; the vertical axis represents blood RNA concentration (μmol/L).

The 10 v/v % blood (50 μL) of each preparation-administered group was mixed with 5 μL of a diethylpyrocarbonate aqueous solution (a 0.1 v/v % mixture of diethylpyrocarbonate in ultrapure water), 10 μL of I.S. solution (0.3 μmol/L of the diethylpyrocarbonate aqueous solution as I.S.), 50 μL of D solution, 10 μL of 2 mmol/L sodium acetate (pH 4.0), and 150 μL of an acidic saturated phenol/chloroform solution (the lower layer of a 1:1 volume ratio mixture of acidic saturated phenol and chloroform was used). The mixture was then centrifuged at 132,000×g for 10 min at 4° C. The supernatant (65 μL) was mixed with 15 μL of a GenTLE solution (GenTLE precipitation carrier (Takara Bio Inc.) diluted 15 times with the diethylpyrocarbonate aqueous solution), and the mixture was allowed to stand at room temperature for at least 10 min after addition of ethanol (200 μL). After 10-min centrifugation (132,000×g) at 4° C., the supernatant was discarded, and 75 v/v % ethanol (200 μL) was added to the precipitate. After 15-min centrifugation (132,000×g) at 4° C., the supernatant was discarded, and the precipitate was air-dried and dissolved in 100 μL of a redissolving solution (a 0.1/0.4/30/1,000 volume ratio mixture of diethylpyrocarbonate/triethylamine/hexafluoroisopropanol/water). The mixture was centrifuged at 132,000×g for 10 min at 4° C., and the supernatant as an analysis sample was quantified using HPLC. The results are shown in FIGS. 3 to 5.

Apparatus
HPLC apparatus: ACQUITY HPLC System (Waters)
Mass spectroscope: API4000 Q TRAP (Applied Biosystems/MDS Sciex)
Analysis software: Analyst 1.4.2 (Applied Biosystems/MDS Sciex)
HPLC Conditions

Example 2

5'-GmUG mAAmG UmCA mACmA UmGC mCUmG CdT-3' (the sugar binding to the base prefaced by d is deoxyriboses, and the sugars binding to the 2nd, 4th, 6th, 8th, 10th, 12th, 14th, 16th, and 18th bases prefaced by m relative to the 5'-end are 2'-O-methyl-substituted riboses) (SEQ ID NO: 15)

5'-mGCmA GmGC mAUmG UmUG mACmU UmCA mCdT-3' (the sugar binding to the base prefaced by d is deoxyriboses, and the sugars binding to the 1st, 3rd, 5th, 7th, 9th, 11th, 13th, 15th, 17th, and 19th bases prefaced by m relative to the 5'-end are riboses substituted with 2'-O-methyl) (SEQ ID NO: 16)

Example 3

5'-GmUG mAAmG UmCA mACmA UmGC mCUmG CdT-3' (the sugar binding to the base prefaced by d is deoxyriboses, and the sugars binding to the 2nd, 4th, 6th, 8th, 10th, 12th, 14th, 16th, and 18th bases prefaced by m relative to the 5'-end are riboses substituted with 2'-O-methyl (SEQ ID NO: 17)

5'-GCA GGC AUG UUG ACU UCA CdT-3' (the sugar binding to the base prefaced by d is deoxyriboses) (SEQ ID NO: 18)

Comparative Example 2

5'-GUG AAG UCA ACA UGC CUG CdT-3' (the sugar binding to the base prefaced by d is deoxyriboses) (SEQ ID NO: 19)

5'-GCA GGC AUG UUG ACU UCA CdT-3' (the sugar binding to the base prefaced by d is deoxyriboses) (SEQ ID NO: 20)

Column: Xbridge C18 (3.5 μm, 2.1 mm I.D.×50 mm, Waters)
Prefilter: Xbridge guard cartridge (3.5 μm, 2.1 mm I.D.×10 mm, Waters)
Column temperature: 65° C.
Mobile phase: triethylamine/hexafluoroisopropanol/water (0.4/30/1000):methanol=93:7 to 75:25
Injection amount: 25 μL
Detection: Mass spectroscope (ionization method: electrospray ionization, negative, ion source temperature: 500° C.)

FIGS. 3 to 5 show that the transition of blood RNA concentration is higher in the mice to which the preparations of Examples 2 and 3 were administered than in the mice to which the preparation of Comparative Example 2 was administered. Specifically, the composition of the present invention in which 1 to 90% of all sugars binding to the bases of sequence X and complementary sequence X' are riboses substituted by a modifying group at 2' position was found to have improved retention in the blood, reduced side effects, or enhanced drug accumulation in tissues or organs containing the expression site of the target gene.

Example 4

The RNA used in Example 4 is a double-stranded RNA containing a sequence consisting of 23 contiguous bases of a BCL2 gene mRNA (hereinafter, sequence $X_4$), and a base sequence (hereinafter, complementary sequence $X_4'$) complementary to sequence $X_4$. [sense: 5'-GmAA mGUmG AmCA mUCmU UmCA mGCmA AmAU mAAdA dC-3' (the sugar binding to the base prefaced by d is deoxyriboses, and the sugars binding to the 2nd, 4th, 6th, 8th, 10th, 12th, 14th, 16th, 18th, 20th, and 22nd bases prefaced by m relative to the 5'-end are riboses substituted with 2'-O-methyl) (SEQ ID NO: 21); antisense: 5'-GUmU UmAU mUUmG CmUG mAAmG AmUG mUCmA CmUU mCmUmU-3' (the sugars binding to the 3rd, 5th, 7th, 9th, 11th, 13th, 15th, 17th, 19th, 21st, 23rd, and 25th to 27th bases prefaced by m relative to the 5'-end are riboses substituted with 2'-O-methyl) (SEQ ID NO: 22)] (hereinafter, 2'-OMe BCL2siRNA Exp.4). Fifty percent of all riboses binding to the bases of sequence $X_4$ and complementary sequence $X_4'$ are riboses substituted with a 2'-O-methyl group. The sense strand and antisense strand were obtained from Hokkaido System Science Co., Ltd., and were annealed to prepare the double-stranded RNA.

DOTAP (manufactured by Avanti Polar Lipids Inc.), PEG-DSPE (manufactured by NOF Corporation) and distilled water (Otsuka Pharmaceutical Co., Ltd.) were mixed such that the ratio of DOTAP/PEG-DSPE/distilled water was 40 mg/16 mg/1 mL, and the mixture was stirred by shaking with a vortex mixer. The suspension so obtained was passed, at 70° C., through a 0.4-μm polycarbonate membrane filter (manufactured by Costar) 10 times and through a 0.2-μm polycarbonate membrane filter (manufactured by Whatman) 5 times and then through a 0.1-μm polycarbonate membrane filter (manufactured by Corning) 10 times and a 0.05-μm polycarbonate membrane filter (manufactured by Whatman) 20 times. The lead particle had an average particles diameter of 72.93 nm as measured by Dynamic light scattering (DLS).

Separately, EPC(NOF Corporation)/PEG-DSPE (NOF Corporation)/ethanol (Wako Pure Chemical Industries, Ltd.)/water (15 mg/3.125 mg/0.625 mL/0.375 mL) were mixed, and a solution containing the constituent components of the lipid bilayer membrane was prepared.

The lead particle dispersion (0.0125 mL) obtained as above was mixed with an aqueous solution (0.00417 mL) obtained by mixing 2'-OMe BCL2siRNA Exp.4 in water in a proportion of 24 mg/1 mL, so as to prepare the complex particles. The dispersion of complex particles was then added to the solution of lipid bilayer membrane constituent components (0.06667 mL), and 0.02083 mL of distilled water was added. After adding 0.00667 mL of a solution of EPC/PEG-DSPE (62.5 mg/62.5 mg/mL) in 40 vol % ethanol, distilled water (0.7758 mL) was gradually added to adjust the ethanol concentration to 5 vol % or less. The resulting lipid particle suspension was isotonized with brine. A preparation was obtained by adjusting the final liquid volume 1 mL with physiological saline (Otsuka Pharmaceutical Co., Ltd.), and thus adjusting the 2'-OMe BCL2siRNA Exp.4 concentration to 0.1 mg/mL.

The lipid particle had an average particles diameter of 87.50 nm as measured by DLS.

Comparative Example 3

The RNA used in Comparative Example 3 is a double-stranded RNA containing sequence $X_4$ and complementary sequence $X_4'$ [sense: 5'-GAA GUG ACA UCU UCA GCA AAU AMA dC-3' (the sugars binding to the bases prefaced by d are deoxyriboses) (SEQ ID NO: 23); antisense: 5'-GUU UAU UUG CUG AAG AUG UCA CUU CUU-3' (SEQ ID NO: 24)] (hereinafter, BCL2siRNA Com.3). The sense strand and antisense strand were obtained from Hokkaido System Science Co., Ltd., and were annealed to prepare the double-stranded RNA.

A preparation was obtained in the same manner as in Example 4, except that 2'-OMe BCL2siRNA Exp.4 was replaced by BCL2siRNA Com.3.

The lipid particle has an average particles diameter of 94.32 nm as measured by DLS.

Test Example 3

Drug solutions (siRNA concentration, 50 μg/mL; 100 μL) containing the preparations obtained in Example 4 and Comparative Example 3 were administered twice to male Balb/c mice (6 weeks of age, CLEA Japan, Inc.) through the tail vein at the 7-day interval (dose, 5 μg/mouse). After the second administration, blood (10 μL) was collected from the tail artery at time point after 3 hours, and mixed with 90 μL of a denaturing solution (4 mol/L guanidine thiocyanate, 25 mmol/L sodium citrate, 1 mmol/L dithiothreitol, 0.5 w/v % sodium N-lauroyl sarcosine; hereinafter, D solution). As a result, a 10 v/v % blood was obtained.

Figure 6:
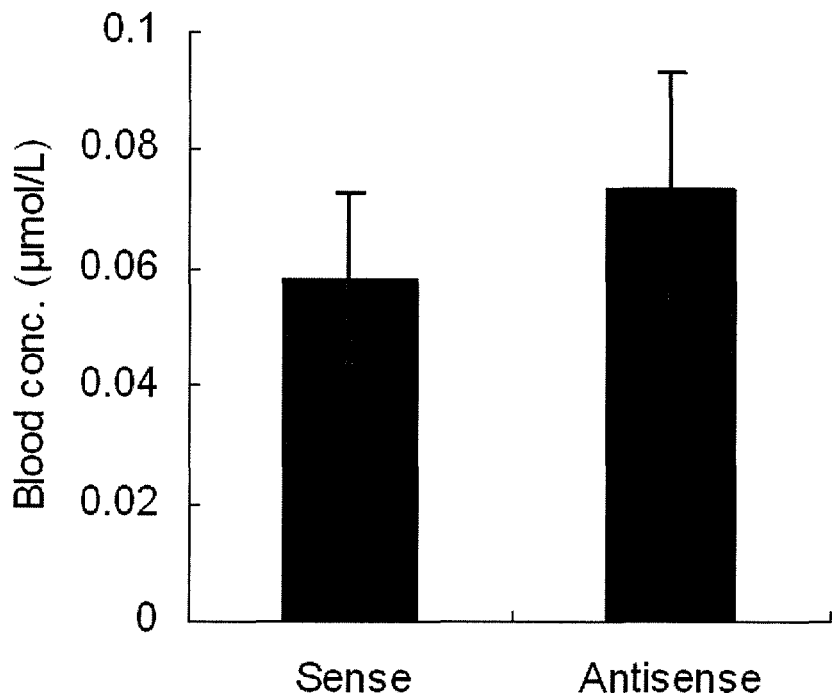
FIG. 6 shows blood RNA concentrations in response to administration of a preparation obtained in Example 4; the vertical axis represents blood RNA concentration (μmol/L).
Figure 7:
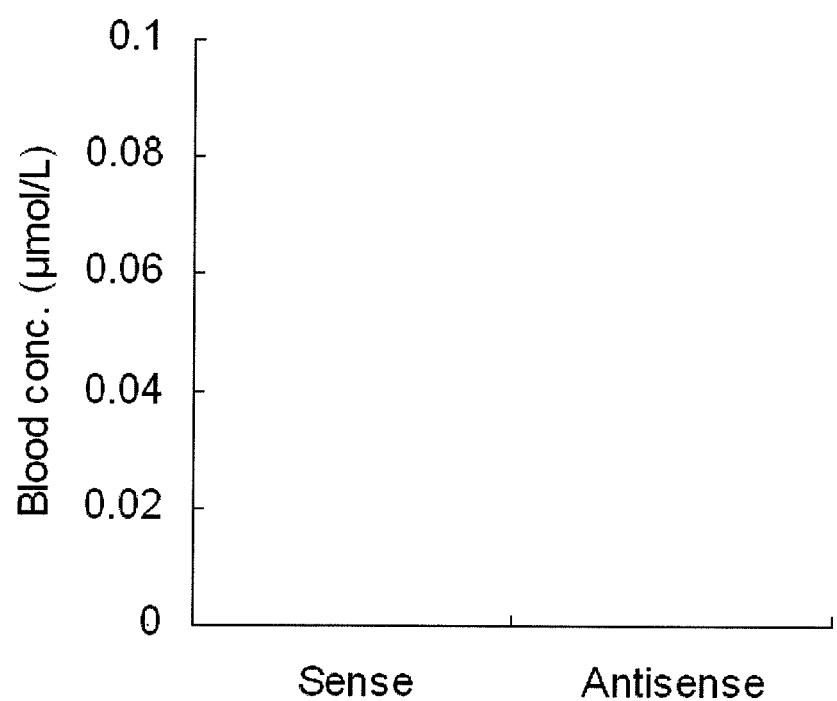
FIG. 7 shows blood RNA concentrations in response to administration of a preparation obtained in Comparative Example 3; the vertical axis represents blood RNA concentration (μmol/L).

The 10 v/v % blood (100 μL) of each preparation-administered group was mixed with 10 μL of a diethylpyrocarbonate aqueous solution (a 0.1 v/v % mixture of diethylpyrocarbonate in ultrapure water), 10 μL of I.S. solution (0.3 μmol/L of the diethylpyrocarbonate aqueous solution as I.S.), 10 μL of 2 mmol/L sodium acetate (pH 4.0), and 150 μL of an acidic saturated phenol/chloroform solution (the lower layer of a 1:1 volume ratio mixture of acidic saturated phenol and chloroform was used). The mixture was then centrifuged at 132,000×g for 10 min at 4° C. The supernatant (30 μL) was mixed with 10 μL of a GenTLE solution (GenTLE precipitation carrier (Takara Bio Inc.) diluted 15 times with the diethylpyrocarbonate aqueous solution), and the mixture was allowed to stand at room temperature for at least 10 min after addition of ethanol (100 μL). After 10-min centrifugation (132,000×g) at 4° C., the supernatant was discarded, and 75 v/v % ethanol (100 μL) was added to the precipitate. After 15-min centrifugation (132,000×g) at 4° C., the supernatant was discarded, and the precipitate was air-dried and dissolved in 50 μL of a redissolving solution (a 0.1/0.4/30/1,000 volume ratio mixture of diethylpyrocarbonate/triethylamine/hexafluoroisopropanol/water). The mixture was centrifuged at 132,000×g for 10 min at 4° C., and the supernatant as an analysis sample was quantified using HPLC. The results are shown in FIGS. 6 and 7.

Apparatus

HPLC apparatus: ACQUITY HPLC System (Waters)
Mass spectroscope: API4000 Q TRAP (Applied Biosystems/MDS Sciex)

Analysis software: Analyst 1.4.2 (Applied Biosystems/MDS Sciex)
HPLC Conditions
Internal Standard Substance (I.S.)

Example 4

5'-GmUG mAUmG UmCA mACmA UmGC mCUmG CdT-3' (the sugar binding to the base prefaced by d is deoxyriboses, and the sugars binding the 2nd, 4th, 6th, 8th, 10th, 12th, 14th, 16th, and 18th bases prefaced by m relative to the 5'-end are riboses substituted with 2'-O-methyl) (SEQ ID NO: 25)

5'-mGCmA GmGC mAUmG UmUG mACmU UmCA mCdT-3' (the sugar binding to the base prefaced by d is deoxyriboses, and the sugars binding to the 1st, 3rd, 5th, 7th, 9th, 11th, 13th, 15th, 17th, and 19th bases prefaced by m relative to the 5'-end are riboses substituted with 2'-O-methyl) (SEQ ID NO: 26)

Comparative Example 3

5'-GUG AAG UCA ACA UGC CUG CdT-3' (the sugar binding to the base prefaced by d is deoxyriboses) (SEQ ID NO: 27)

5'-GCA GGC AUG UUG ACU UCA CdT-3' (the sugar binding to the base prefaced by d is deoxyriboses) (SEQ ID NO: 28)

Column: Xbridge C18 (3.5 μm, 2.1 mm I.D.×50 mm, Waters)
Prefilter: Xbridge guard cartridge (3.5 μm, 2.1 mm I.D.×10 mm, Waters)
Column temperature: 65° C.
Mobile phase: triethylamine/hexafluoroisopropanol/water (0.4/30/1000):methanol=93:7 to 75:25
Injection amount: 25 μL
Detection: Mass spectroscope (ionization method: electrospray ionization, negative, ion source temperature: 500° C.)

FIGS. 6 and 7 show that the transition of blood RNA concentration is higher in the mice to which the preparation of Example 4 was administered than in the mice to which the preparation of Comparative Example 3 was administered. Specifically, the composition of the present invention in which 1 to 90% of all sugars binding to the bases of sequence X and complementary sequence X' are riboses substituted by a modifying group at 2' position was found to have improved retention in the blood, reduced side effects, or enhanced drug accumulation in tissues or organs containing the expression site of the target gene.

INDUSTRIAL APPLICABILITY

By administering the composition of the present invention that comprises a lipid particle encapsulating an RNA that contains a sequence consisting of 15 to 30 contiguous bases of a target gene mRNA and a base sequence complementary to the sequence to a mammal or the like, the expression of the target gene can be suppressed.

SEQUENCE LISTING FREE TEXT

SEQ ID NO: 1 siRNA sense of exp.1
SEQ ID NO: 2 siRNA antisense of exp.1
SEQ ID NO: 3 siRNA sense of com.1
SEQ ID NO: 4 siRNA antisense of com.1
SEQ ID NO: 5 IS for siRNA sense of exp.1
SEQ ID NO: 6 IS for siRNA antisense of exp.1
SEQ ID NO: 7 IS for siRNA sense of com.1
SEQ ID NO: 8 IS for siRNA antisense of com.1
SEQ ID NO: 9 siRNA sense of exp.2
SEQ ID NO: 10 siRNA antisense of exp.2
SEQ ID NO: 11 siRNA sense of exp.3
SEQ ID NO: 12 siRNA antisense of exp.3
SEQ ID NO: 13 siRNA sense of com.2
SEQ ID NO: 14 siRNA antisense of com.2
SEQ ID NO: 15 IS for siRNA sense of exp.2
SEQ ID NO: 16 IS for siRNA antisense of exp.2
SEQ ID NO: 17 IS for siRNA sense of exp.3
SEQ ID NO: 18 IS for siRNA antisense of exp.3
SEQ ID NO: 19 IS for siRNA sense of com.2
SEQ ID NO: 20 IS for siRNA antisense of com.2
SEQ ID NO: 21 siRNA sense of exp.4
SEQ ID NO: 22 siRNA antisense of exp.4
SEQ ID NO: 23 siRNA sense of com.3
SEQ ID NO: 24 siRNA antisense of com.3
SEQ ID NO: 25 IS for siRNA sense of exp.4
SEQ ID NO: 26 IS for siRNA antisense of exp.4
SEQ ID NO: 27 IS for siRNA sense of com.3
SEQ ID NO: 28 IS for siRNA antisense of com.3
SEQ ID NO: 29 bcl2 mRNA
[SEQUENCE LISTING]

The invention claimed is:

1. A method for improving blood RNA concentration after a second administration to a mammal of a composition comprising a RNA-encapsulated lipid particle comprising a polyethylene glycolated lipid, a polyethylene glycol sorbitan fatty acid ester or a polyethylene glycol fatty acid ester, wherein the RNA comprises a sequence X consisting of 15 to 30 contiguous bases of a target gene mRNA and a base sequence X' complementary to the sequence X, comprising twice administering to a mammal the composition
wherein 10 to 75% of all sugars in the RNA binding to the bases of the sequence X and the base sequence X' are ribose substituted by a modifying group selected from the group consisting of 2'-fluoro, 2'-O-methyl, 2'-O-ethyl.

2. The method according to claim 1, wherein the lipid particle is a lipid particle having a size that allows intravenous administration.

3. The method according to claim 2, wherein the RNA is an RNA having an action of suppressing the expression of the target gene by utilizing RNA interference (RNAi).

4. The method according to claim 3, wherein the target gene is a gene associated with a tumor or inflammation.

5. The method according to claim 3, wherein the mRNA is either human mRNA or mouse mRNA.

6. The method according to claim 3, wherein the RNA-encapsulated lipid particle comprises:
a complex particle that contains a lead particle and the RNA as constituent components, and
a lipid bilayer membrane for coating the complex particle, wherein constituent components of the lipid bilayer membrane are soluble in a polar organic solvent, and wherein the constituent components of the lipid bilayer membrane, and the complex particle are dispersible in a liquid that contains the polar organic solvent in a specific concentration.

7. The method according to claim 6, wherein the polar organic solvent is an alcohol.

8. The method according to claim 6, wherein the polar organic solvent is ethanol.

9. The method according to claim 6, wherein the lead particle contains a cationic substance, and wherein the lipid bilayer membrane contains, as constituent components, a neutral lipid, and a lipid derivative, a fatty acid derivative, or an aliphatic hydrocarbon derivative of a water-soluble substance.

10. The method according to claim 3, wherein the RNA-encapsulated lipid particle is a lipid particle that comprises: a complex particle that contains a cationic substance-containing lead particle and the RNA as constituent components, and a lipid bilayer membrane for coating the complex particle, and wherein the lipid bilayer membrane contains, as constituent components, a neutral lipid, and a lipid derivative, a fatty acid derivative, or an aliphatic hydrocarbon derivative of a water-soluble substance.

* * * * *